United States Patent [19]

Tanaka et al.

[11] Patent Number: 5,077,046
[45] Date of Patent: Dec. 31, 1991

[54] POLYPRENYL COMPOSITION OR COMPOUNDS AND PROCESS FOR THE PRODUCTION THEREOF

[75] Inventors: Yasuyuki Tanaka, Hachioji; Koichi Ibata; Masao Mizuno, both of Kurashiki; Yoichi Ninagawa, Hasaki; Takashi Nishida, Kurashiki, all of Japan

[73] Assignee: Kuraray Co., Ltd., Okayama, Japan

[21] Appl. No.: 410,588

[22] Filed: Sep. 21, 1989

Related U.S. Application Data

[60] Division of Ser. No. 81,735, Aug. 5, 1987, Pat. No. 4,886,904, which is a division of Ser. No. 654,526, Sep. 25, 1984, Pat. No. 5,012,018, which is a continuation-in-part of Ser. No. 371,487, Apr. 23, 1982, abandoned, which is a continuation-in-part of Ser. No. 324,636, Nov. 24, 1981, abandoned.

[30] Foreign Application Priority Data

Nov. 28, 1980 [JP] Japan ................................ 55-168747

[51] Int. Cl.$^5$ .................. C07C 29/86; C07C 33/02; C07C 67/58; C07C 69/007
[52] U.S. Cl. .................. 424/195.1; 560/172; 560/249; 560/261; 560/129
[58] Field of Search ............... 560/249, 261, 129, 172; 424/195.1

[56] References Cited

U.S. PATENT DOCUMENTS

| | | | |
|---|---|---|---|
| 4,668,820 | 5/1987 | Ibata | 560/248 |
| 4,762,829 | 8/1988 | Yamatsu | 514/218 |
| 4,886,904 | 12/1989 | Tanaka | 560/249 |
| 4,888,439 | 12/1989 | Yamatsu | 560/129 |

FOREIGN PATENT DOCUMENTS

| | | | |
|---|---|---|---|
| 085275 | 5/1982 | Japan | 560/248 |
| 093432 | 5/1982 | Japan | 560/248 |

*Primary Examiner*—Ronald W. Griffin
*Assistant Examiner*—Ralph G. Gitomer
*Attorney, Agent, or Firm*—Wenderoth, Lind & Ponack

[57] ABSTRACT

A polyprenyl composition consisting essentially of a mixture of polyprenyl compounds represented by the following formula

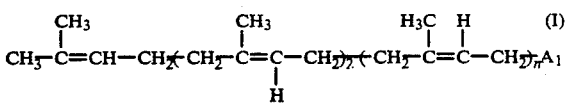

wherein $A_1$ represents a hydroxyl or acetyloxy group,

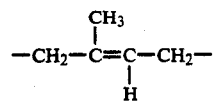

represents a trans-isoprene unit,

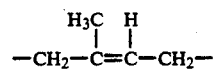

represents a cis-isoprene unit, and n is an integer of from 11 to 19, said mixture containing substantial amounts of at least three compounds of formula (I) wherein n represents 14, 15 and 16 respectively as essential ingredients in a total amount of at least 70% by weight based on the weight of the mixture; and new compounds derived from the polyprenyl compounds of formula (I). These composition and compounds are useful for the synthesis of mamammalian dolichols. The polyprenyl composition can be prepared by extracting the leaves of *Ginkgo biloba* or *Cedrus deodara* with an oil-soluble organic solvent; if required, hydrolyzing the extract; and subjecting the extract to one or more of chromatography, fractional dissolution, fractional refrigerating precipitation and molecular distillation, thereby separating and recovering a fraction having a specified Rf value in silica thin-layer chromatography.

3 Claims, No Drawings

POLYPRENYL COMPOSITION OR COMPOUNDS AND PROCESS FOR THE PRODUCTION THEREOF

This application is a divison of U.S. application Ser. No. 07/081,735 filed Aug. 5, 1987, now U.S. Pat. No. 4,886,904, which is a division of U.S. application Ser. No. 06/654,526 filed Sept. 25, 1984, now U.S. Pat. No. 5,012,018 which is a continuation-in-part of U.S. application Ser. No. 06/371,487, filed Apr. 23, 1982, abandoned Sept. 25, 1984, which is a continuation-in-part of U.S. application Ser. No. 06/324,636, filed Nov. 24, 1981, abandoned Oct. 1, 1982.

This invention relates to a novel polyprenyl composition or compounds. More specifically, this invention pertains to a novel polyprenyl composition composed to a mixture of polyprenyl homologs which can be extracted from *Ginkgo biloba* or *Cedrus deodara*, novel polyprenyl compounds which can be derived from the aforesaid polyprenyl homologs, a process for the production of said polyprenyl composition or compounds, and use of such a composition or compounds in the synthesis of mammalian dolichols.

Dilichols were first isolated in 1960 from human kidneys, pig livers, etc. by J. F. Pennock et al. [see Nature (London) 186, 470 (1960)]. Later, they ascertained that the dolichols are a mixture of polyprenol homologs having the composition of the following general formula,

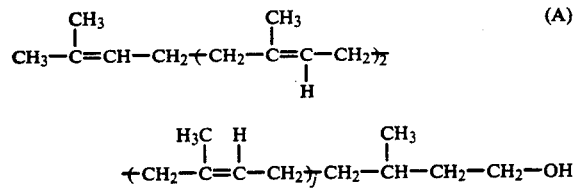

wherein

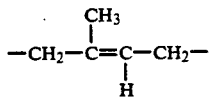

represents a trans-isoprene, unit, and

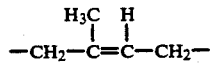

represents a cis-isoprene unit (the same definitions apply throughout the present specification), and the number j of cis-isoprene units in the above formula generally distributes between 12 to 18 and three homologs in which j is 14, 15 and 16 are present in major proportions [R. W. Keenan et al., Biochemical Journal, 165, 405 (1977)]. It is also known that dolichols are distributed widely in mammals, and performs a very important function in maintaining the lives of organisms. For example, J. B. Harford et al. showed by in vitro tests using the brain white matter of calves or pigs that exogenous dolichols promote in-take of carbohydrates such as mannose into lipid, and consequently increase the formation of glycoproteins which are important for maintaining the lives or organisms [Biochemical and Biophysical Research Communication, 76, 1036 (1977)]. Since the effect of dolichols to take carbohydrates into lipid is remarkable in mature animals as compared with those in the activity growing stage, the action of the dolichols has attracted attention for its possible prevention of aging.

R. W. Keenan et al. state that it is important for organisms which rapidly keep growing, for example, those in the infant stage, to take dolichols extraneously so as to supplement the dolichols obtained by biosynthesis within their own body [Archives of Biochemistry and Biophysics, 179, 634 (1977)].

Akamatsu et al. determined the quantity of dolichols in the regenerated liver of a rat and found that the quantity determined is much smaller than that in normal liver and the function of the liver tissues to synthesize glycoproteins is drastically reduced and that the addition of exogenous dolichols improves the reduced function of glycoprotein synthesis (published in the 1981 conference of the Japanese Society of Biochemistry).

In this way, the dolichols are very important substances for organisms, and it is strongly desired to develop their use as medicines or intermediates for their synthesis, cosmetics, etc.

However, since dolichols have hitherto been difficult to obtain, sufficient research works have been impossible. For example, only about 0.6 g at most of dolichols can be obtained from 10 kg of pig liver through complicated separating procedures [see J. Burgos et al., Biochemical Journal, 88, 470 (1963)].

On the other hand, it is extremely difficult by the present day techniques of organic synthesis to produce dolichols by a wholly synthetic process, as can be seen in the light of their complex and unique molecular structure. It would be advantageous if dolichols could be obtained by simple synthetic chemical treatments from naturally occurring intermediates. Such convenient natural substances, however, have not been discovered to date. It has been known that polyprenol compounds can be extracted from various plants, and so far, the following polyprenols have been successfully extracted.

(1) Solanesol

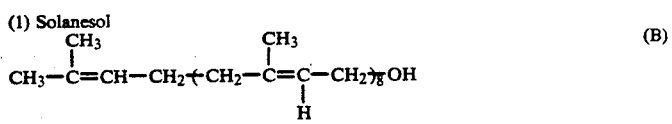

(2) Ficaprenols

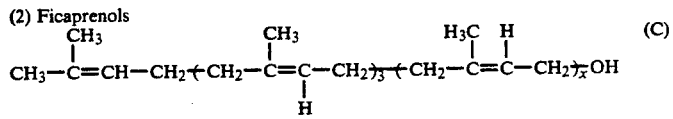

x = 5–9

(3) Betulaprenols

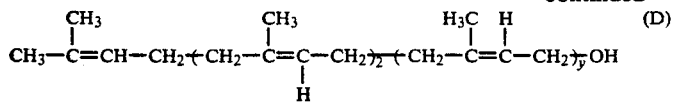

y = 3-6
y = 4-6

The betulaprenols have a structure similar to the dolichols in that two trans-isoprene units are connected to the omega-terminal isoprene unit and a cis-isoprene unit is linked to these trans-isoprene units. However, the betulaprenols so far known contain up to six cis-isoprene units at most, and in order to synthesize dolichols containing homologs having 14, 15 and 16 cis-isoprene units respectively as major components from these betulaprenols, it is necessary to link at least 8 isoprene units while maintaining them in cis-form. This procedure is almost impossible by the present-day organic synthetic techniques.

Recently, K. Hannus et al. reported that a polyisoprenyl fraction in an amount of about 1% dry weight was isolated from the needles of *Pinus sylvestris*, and the fraction consisted of polyisoprenyl acetates with 10 to 19 isoprene units predominantly in the cis-configuration. However, the pinoprenol fraction contains homologs having 15 and 16 isoprene units as major components, and only traces of homologs with 17, 18 and 19 isoprene units which are the main components of mammalian dolichols [Phytochemistry, 13, 2563 (1974)]. The Hannus et al. article does not give details about the trans- and cis-configurations of the pinoprenol homologs. Even if the pinoprenol fraction has the same trans- and cis-configurations as mammalian dolichols, it is necessary, for conversion into mammalian dolichols, to link at least two cis-isoprene units while maintaining them in cis-form and further bond a saturated isoprene unit to the alpha-terminal. Evidently, this presents great synthetic difficulties.

D. F. Zinkel et al. reported that the extracts of *Pinus strobus* needles contain a $C_{90}$ polyprenol containing 18 isoprene units or a homologous series of polyprenols averaging 18 units [Phytochemistry, 11, 3387 (1972)]. Their analysis, however, are based only on NMR and are very rough. When the inventors of the present application traced this experiment, they found that the polyprenol fraction extracted from the needles of *Pinus strobus* containing a homolog containing 17 isoprene unit as a major component. In order to synthesize mammalian dolichols from the polyprenyl fraction isolated from the needles *Pinus strobus*, it is necessary to introduce at least one cis-isoprene unit while maintaining it in cis-form, and synthetic difficulties are still anticipated.

The present invention searched various plants for polyprenyl compounds which have the same number of isoprene units of trans- and cis-configurations as mammalian dolichols and therefore do not require a difficult operation of introducing cis-isoprene units while maintaining them in the cis-configuration, and analyzed extracts from various plants. These investigations have led to the surprising discovery that the polyprenyl fraction (or composition) extracted from *Ginkgo biloba* or *Cedrus deodara* shows a very similar distribution of polyprenyl homologs to that of polyprenyl homologs in mammalian dolichols except that it does not contain a saturated isoprene unit at the alpha-terminal, and therefore that the extracted polyprenyl fraction is very suitable as an intermediate for synthesis of mammalian dolichols.

According to one aspect of this invention, there is provided a novel polyprenyl composition (fraction) consisting essentially of a mixture of polyprenyl compounds represented by the following formula

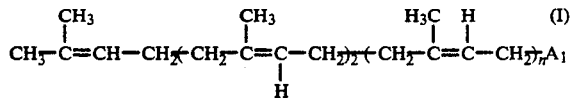

wherein $A_1$ represents a hydroxyl or acetyloxy group,

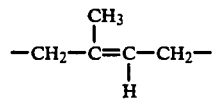

represents a trans-isoprene unit,

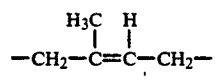

represents a cis-isoprene unit, and n is an integer of from 11 to 19, said mixture containing substantial amounts of at least three compounds of formula (I) wherein n represents 14, 15 and 16 respectively as essential ingredients in a total amount of at least 70% by weight based on the weight of the mixture.

According to another aspect of the invention, the novel polyprenyl composition (or fraction) can be produced by extracting the leaves of *Ginkgo biloba* or *Cedrus deodara* with an oil-soluble organic solvent; if required, hydrolyzing the extract; and subjecting the extract to one or more of chromatography, fractional dissolution, fractional refrigerating precipitation and molecular distillation, thereby separating and recovering a fraction which shows an Rf value of from 0.18 to 0.25 and/or from 0.50 to 0.55 in thin-layer chromatography (developed 10 cm) carried out in a TLC plate of Merck Co. precoated with silica gel (60 $F_{254}$ to a layer thickness of 0.25 mm with a mixture of n-hexane and ethyl acetate in a volume ratio of 9:1 as a developing solvent under such conditions that solanesyl acetate as a standard substance shows an Rf value of from 0.40 to 0.45.

The polyprenyl composition or fraction and the process for its production will be described below in greater detail.

*Ginkgo biloba* used as a raw material for extraction of the polyprenyl fraction in accordance with this invention is a plant belonging to Division Spermatophyta, Subdivision Gymnospermae, Class Ginkgopsida, Order Ginkgoales, Family Ginkgoaceae which occurs mainly in East Asia, especially Japan, China, and Korea. *Cedrus deodara*, another raw material used in this invention, is a plant belonging to Division Spermatophyta, Subdivision Gymnospermae, Class Coniferopsida, Order Coniferales, Family Pinaceae which distributes widely in the Temperate and Frigid Zones. In the present invention, the leaves of these plants are used as the raw materials.

The leaves of *G. biloba* or *C. deodara* which can be used in this invention may range from young green leaves to completely yellowed leaves, and the fallen leaves may also be used. The leaves to be treated by the process of this invention may be used undried or after drying. Generally, the dried leaves are preferred. The degree of drying of the leaves should advantageously correspond to a water content, based on the weight of the dried leaves, of less than about 30%, preferably less than about 10%. Preferably, the leaves are extracted after they have been crushed. This increases the area of contact with the extracting solvent, and results in an increased efficiency of extraction.

The polyprenyl homologs of formula (I) are contained in fairly high concentrations generally in the form of a free alcohol and/or acetic acid ester. In order to extract the polyprenol homologs from the leaves of these plants effectively, the use of oil-soluble organic solvents capable of well dissolving the polyprenyl homologs is convenient.

Suitable oil-soluble organic solvents that can be used in this invention have a dielectric constant ($\epsilon$) of not more than 32.7, preferably not more than 25.0, especially preferably not more than 20.7. Specifically, solvents exemplified below are used either singly or as a mixture of two or more.

(a) Hydrocarbons such as petroleum ether, pentane, hexane, heptane, benzene, toluene and xylene.

(b) Halogenated hydrocarbons such as chloroform, methylene chloride, carbon tetrachloride, tetrachloroethane, perchloroethylene and trichloroethylene.

(c) Esters such as methyl acetate, ethyl acetate and ethyl propionate.

(d) Ethers such as diethyl ether, diisopropyl ether, tetrahydrofuran and dioxane.

(e) Ketones such as acetone, methyl ethyl ketone diethyl ketone and diisopropyl ketone.

(f) Alcohols such as methyl alcohol, ethyl alcohol, propyl alcohol, and butyl alcohol.

The solvent should desirably extract the desired polyprenyl compounds of formula (I) selectively with a high efficiency, while permitting minimization of extraction of other substances. From this standpoint, the hydrocarbons, halogenated hydrocarbons, esters, and ethers having low polarity such as diethyl ether and diisopropyl ether, and ketones are especially suitable among the above-exemplified solvents.

The amount of the extracting solvent is not critical, and can be varied widely depending upon the type of the solvent, the type or condition of the leaves to be extracted, etc. Generally, it is advantageous that the solvent is used in an amount of about 1 to about 100 parts by weight, preferably 5 to 50 parts by weight, more preferably 10 to 30 parts by weight, per part (based on the dry weight) of the leaves of *Gingko biloba* or *Cedrus deodara*.

The extraction can be carried out by dipping the leaves in the solvent, and if required, stirring the solvent continuously or intermittently. The temperature during the extraction is neither critical, and can be varied widely depending upon the extracting conditions such as the type or amount of the solvent used. Generally, the extracting temperature is from about 0° C. to the refluxing temperatures of the solvent. Usually, room temperature suffices. Advantageously, under these conditions, the extraction can be carried out for a period of 1 to 10 days.

After the extracting treatment, the leaves and other solid components are removed from the dipping solution and if required, the solvent is removed to form a concentrate. The extract is subjected to a separating step consisting of one or more of chromatography, fractional dissolution, fractional refrigerating precipitation and molecular distillation, whereby the desired polyprenyl fraction is recovered.

In the separating step, the formation of the fraction of polyprenyl compounds is confirmed by determining whether a spot exists at an Rf value of from 0.18 to 0.25 [when $A_1$ in formula (I) represents a hydroxyl group] and/or from 0.50 to 0.55 [when $A_1$ in formula (I) represents an acetyloxy group] in thin-layer chromatography which is carried out on a TLC plate of Merck Co. precoated with silica $60F_{254}$ to a layer thickness of 0.25 mm with a mixture of n-hexane and ethyl acetate in a volume ratio of 9:1 as a developing solvent (developed 10 cm) under such conditions that solanesyl acetate as a standard substance shows an Rf value of from 0.40 to 0.45 in the thin-layer chromatography. It should be understood that in the following description, the Rf values of thin-layer chromatography denote those which are measured under the aforesaid conditions unless otherwise specified.

The operations of the chromatography, fractional dissolution, fractional refrigerating precipitation and molecular distillation used in the step of separating the aforesaid extract are known per se, and in the present invention, too, these methods can be carried out in accordance with known procedures. For the details of these methods, literature references will be cited in lieu of describing them at length. Only those items which need special care will be described below.

(A) Chromatography

For details, reference may be made to H. Heftman "Chromatography," Reinhold Publishing Co., New York (1961).

When the amount of the extract is small, thin-layer chromatography or liquid chromatography is suitable. For treatment of a large amount of the extract, column chromatography is suitable.

Examples of suitable chromatography carriers are silica gel, alumina, Florisil, Celite, activated carbon, and cellulose. Silica gel is especially preferred.

Examples of the developing solvent used in the separating operation on a silica gel column include hexane/ethyl acetate (volume ration from 98:2 to 80:20), hexane/diisopropyl ether (volume ratio from 95:5 to 80:20), petroleum ether/methyl acetate (volume ratio from 98:2 to 80:20), petroleum ether/isopropyl alcohol (volume ratio from 99:1 to 90:10), benzene/diethyl ether (volume ratio from 95:5 to 80:20), benzene/ethyl acetate (volume ratio from 98:2 to 80:20), and chloroform.

(B) Fractional Dissolution

For details, reference may be made to L. C. Craig, "Techniques of Organic Chemistry", Vol. 3, Interscience (1951).

The polyprenyl compounds of formula (I) are easily soluble in non-polar solvents such as pentane and hexane, but are sparingly soluble in polar solvents such as methanol or water. Hence, the polyprenyl compounds of formula (I) can be purified by the fractional dissolving method utilizing differences in solubility in these solvents. For example, a crude product such as a concentrate of the extract is dissolved in the aforesaid nonpolar solvent, and then washed with a polar solvent which is immiscible with the nonpolar solvent, whereby impurities easily soluble in the polar solvent can be drastically removed. Suitable nonpolar solvents used in this method are, for example, hydrocarbons such as petroleum ether, pentane, hexane, heptane, benzene and toluene and halogenated hydrocarbons such as methylene chloride and chloroform. Suitable polar solvents immiscible with such nonpolar solvents are, for example, water and methanol.

(C) Fractional Refrigerating Precipitation

For details, reference may be made to E. W. Berg, Physical and Chemical Methods of Separation, Chapters 14 and 15, McGraw-Hill, New York (1963).

The polyprenyl compounds of formula (I) solidify at about $-10°$ C. or less. Hence, the polyprenyl compounds of formula (I) can be purified by allowing the extract to stand at a temperature of not more than $-10°$ C., preferably $-15°$ to $-30°$ C., to solidify the desired compounds, and removing the impurities which do not solidify at these temperatures by a solid-liquid separating technique. The polyprenyl compounds, however, do not have good crystallinity and become a waxy solid. Accordingly, they are difficult to purify completely only by this method. Preferably, therefore, this method is used in combination with another purifying method.

(D) Molecular Distillation

For details, reference may be made to G. Burrows, Molecular Distillation, Clarendon Press, Oxford (1960).

Since the compounds of formula (I) have a high molecular weight, they can be separated from low-molecular-weight impurities by the molecular distillation method. For example, the extract is subjected to molecular distillation at 100° to 250° C. under a vacuum of $10^{-3}$ to $10^{-5}$ mmHg to divide it into a low-molecular-weight fraction and a high-molecular-weight fraction. The desired compounds are retained in the high-molecular-weight fraction, and the low-molecular-weight impurities can be removed effectively.

When a sufficiently pure polyprenyl fraction cannot be obtained by each of these separating methods, two or more of these separating methods may be used in combination. For example, there can be used a combination of chromatography and fractional dissolution, a combination of chromatography, fractional refrigerating precipitation and fractional dissolution, a combination of chromatography, fractional refrigerating precipitation, fractional dissolution and molecular distillation, a combination of chromatography, molecular distillation and fractional dissolution, a combination of chromatography and molecular distillation, a combination of molecular distillation and fractional dissolution, and a combination of molecular distillation, fractional dissolution and fractional refrigerating precipitation.

As a result of the separating step, a fraction having an Rf value of from 0.18 to 0.25, and/or from 0.50 to 0.55 in thin-layer chromatography can be isolated and recovered. The fraction having an Rf value of 0.18 to 0.25 consists essentially of a mixture of homologs of formula (I) in which $A_1$ represents a hydroxyl group, and the fraction having an Rf value of from 0.50 to 0.55 consists essentially of homologs of formula (I) in which $A_1$ represents an acetyloxy group.

The resulting fraction can be separated into the individual homologs by subjecting it further, for example, to high-performance partition liquid chromatography.

Prior to submitting the extract to the aforesaid separating operation, the extract may be hydrolyzed as required to convert homologs of formula (I) in which $A_1$ represents an acetyloxy group into homologs of formula (I) in which $A_1$ represents a hydroxyl group. Of course, the hydrolysis may also be carried out on a fraction having an Rf value of 0.50 to 0.55 obtained by the separating operation. The hydrolysis can be performed by any usual methods known in the hydrolysis of known fatty acid esters. For example, about 5 to about 50 parts by weight of the extract or the fraction is added to 100 parts by weight of a solution of sodium hydroxide or potassium hydroxide in aqueous methanol or ethanol (the alkali metal hydroxide concentration of preferably about 0.1 to 30% by weight), and reacted at about 25° to 90° C. for about 0.5 to 5 hours.

In the polyprenyl fraction separated and recovered by the method described hereinabove, the fraction having an Rf value of 0.18 to 0.25 consists essentially of a mixture of polyprenol homologs in which $A_1$ represents a hydroxyl group, and the fraction having an Rf value of 0.50 to 0.55 consists essentially of a mixture of polyprenyl acetate homologs of formula (I) in which $A_1$ represents an acetyloxy group. The ratio of the former to the latter in the extract is in the range of from 1:100 to 1:5. The distribution pattern of the polyprenol or polyprenyl acetate homologs is nearly the same for these fractions. The distribution pattern is nearly constant irrespective of the type of the plant used as a raw material, the stage of growth of the leaves, the time of harvesting, the region of growth, etc.

The fraction generally contains substantial amounts of at least three compounds, i.e. a compound of formula (I) in which n is 14 (to be referred to as polyprene-14), a compound of formula (I) in which n is 15 (to be referred to as polyprene-15), and a compound of formula (I) in which n is 16 (to be referred to as polyprene-16). The total amount of the three compounds is at least 70% by weight, preferably at least 75% by weight, based on the weight of the fraction.

Generally, the fraction contains polyprene-15 in the highest proportion. The content of polyprene-15 is usually 30 to 50% by weight, typically 42 to 47% by weight, based on the weight of the fraction.

Generally, the fraction contain polyprene-14, polyprene-15 and polyprene-16 in a unique quantitative relation. Let the contents of these compounds be a, b and c% by weight respectively, the quantitative relation is usually $b>a>c$.

The fraction contains generally 20 to 35% by weight, typically 23 to 32% by weight, of polyprene-14, and generally 10 to 25% by weight, typically 11 to 20% by weight, of polyprene-16.

The polyprenyl composition (or fraction) provided by this invention is characteristic in that the distribution pattern of polyprenol homologs is very similar to that of mammalian dolichols, that is the distribution pattern of n in formula (I) is very similar to that of j in formula (A). The distribution pattern of the polyprenol homologs is shown blow against that of pig dolichols (the distribution pattern of human dolichols is much the same as that of pig dolichols). The parenthesized figures show typical ranges.

TABLE 1

| n in formula (I) and j in formula (A) | Content (wt. %) | |
|---|---|---|
| | Polyprenyl composition of the invention | Pig dolichols |
| 11 | 0-3 (0-2) | 0.43 |
| 12 | 0.1-6 (0.1-6) | 0.60 |
| 13 | 4-17 (5-14) | 4.38 |
| 14 | 20-35 (23-32) | 25.59 |
| 15 | 30-50 (32-47) | 46.01 |
| 16 | 10-25 (11-20) | 18.79 |
| 17 | 2-10 (2-6) | 3.41 |
| 18 | 0.1-5 (0.1-2) | 0.72 |
| 19 | 0-3 (0-1.5) | 0.06 |

The polyprenyl composition provided by this invention does not substantially contain components other than the polyprenyl homologs of formula (I) shown in Table 1 above, and the average value of n is usually in the range of from 14.25 to 15.25.

As can be seen from the distribution pattern of the polyprenyl homologs shown in Table 1 and from a comparison of formula (I) with formula (A), the polyprenyl composition provided by this invention can be converted to mammalian dolichols by linking one saturated isoprene unit to the alpha-end of each of the polyprenyl compounds in the composition. The problem of cis- or trans-configuration requires no consideration in regard to the saturated isoprene unit to be linked, and in linking the saturated isoprene unit, no difficulty arises in the reaction operation. Accordingly, the polyprenyl composition provided by this invention is a very important intermediate for the synthesis of mammalian dolichols.

In converting the polyprenyl composition of the invention into mammalian dolichols, the composition may be used as such, or as required, after the composition has been separated into the individual polyprenyl compounds. It should be understood therefore that although the following description refers to reactions of the polyprenyl compounds of formula (I), it may be read by replacing the polyprenyl compounds by the polyprenyl composition having the aforesaid distribution pattern.

In converting the polyprenyl compounds of formula (I) into the dolichols of formula (A), the compounds of formula (I) may be reacted with a reagent for introduction of a saturated isoprene unit, either as such or after A₁ in formula (A) has been replaced by another reactive leaving atom or group.

Thus, according to still another aspect of this invention, there is provided a process for producing a mammalian dolichol or its precursor of the following formula

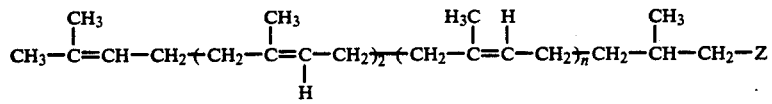

wherein Z represents a group of the formula —CH₂OH or its functional precursor group, n is an integer of 11 to 19,

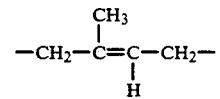

represents a trans-isoprene unit, and

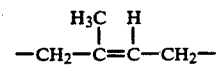

represents a cis-isoprene unit, which comprises reacting a polyprenyl compound of the following general formula

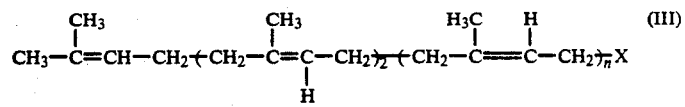

(III)

wherein X represents a leaving atom or group, n is as defined above, and the expression of the trans- and cis-isoprene units is as defined above, with a compound of the general formula $$Y-CH_2-\underset{\underset{CH_3}{|}}{CH}-CH_2-Z \qquad (IV)$$

wherein Y represents a lithium atom or MgHal in which Hal is a halogen atom, and Z is as defined above, to form a compound of formula (V); and when Z represents the functional precursor group, converting it, if required, into —CH₂OH.

The leaving atom or group X in formula (III) includes not only a hydroxyl group and an acetyloxy group, but also any other atoms or groupings which have the property of being split off by reaction with the MgHal or lithium atom Y, whereby they perform substitution reaction with the carbon atom to which Y is bonded, on the carbon atom to which X was bonded. Preferably, such leaving atom or group is selected from the class consisting of halogen atoms and groups of the formulae

—OCOR₁, —OR₂, —OPO(OR₃)₂, —SOR₃, —SO₂R₃,

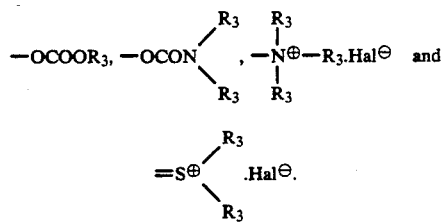

In the above formulae, R₁ represents a hydrogen atom, a methyl group substituted by 1 to 3 fluorine or chlorine atoms, an alkyl or alkenyl group having 2 to 18 carbon atoms, an aryl group having 6 to 10 carbon atoms or an aralkyl group having 7 to 11 carbon atoms;

$R_2$ represents a lower alkyl group, a lower alkenyl group, an aryl group having 6 to 10 carbon atoms, a pyridyl group, a thiazolyl group, a thiazolinyl group, or an oxazolyl group; $R_3$ represents a lower alkyl group, an aryl group having 6 to 10 carbon atoms, or an aralkyl group having 7 to 11 carbon atoms; Q represents an oxygen or sulfur atom; and Hal represents a halogen atom.

In the present specification and the appended claims, the term "lower" as used to qualify a group or a compound means that the group or compound so qualified has up to 8 carbon atoms, preferably up to 4 carbon atoms.

Examples of the "methyl group substituted by 1 to 3 fluorine or chlorine atoms" in the above definition are $-CH_2F$, $-CHF_2$, $-CF_3$, $-CH_2Cl$, $-CHCl_2$, and $-CCl_3$, and $-CH_2F$, $-CF_3$, and $-CH_2Cl$ are preferred.

The alkyl and alkenyl groups may be linear, branched linear, or cyclic. Examples of the alkyl group are methyl, ethyl, n-propyl, isopropyl, n-butyl, sec-butyl, isobutyl, tert-butyl, n-pentyl, isoamyl, n-hexyl, n-octyl, n-decyl, n-dodecyl, n-undecyl, stearyl, cyclopentyl, cyclohexyl, and cycloheptyl. Examples of the alkenyl group include 3-butenyl, 3-pentenyl, 4-pentenyl, geranyl, farnesyl, and oleyl.

The "alkyl or alkenyl groups having 2 to 18 carbon atoms" represented by $R_1$ are preferably alkyl groups having 2 to 6 carbon atoms and alkenyl groups having 4 to 6 carbon atoms. As the "lower alkyl group" and the "lower alkenyl group" represented by $R_2$ and $R_3$ respectively, methyl, ethyl, n-propyl, i-propyl and butyl, and vinyl and 3-butenyl are especially preferred.

The "aryl groups having 6 to 10 carbon atoms" include a phenyl group, a phenyl group whose benzene ring is substituted by 1 to 3 lower alkyl groups, such as tolyl or xylyl, and a naphthyl group. The "aralkyl groups having 7 to 11 carbon atoms" include lower alkyl groups substituted by a substituted or unsubstituted phenyl group, such as benzyl, phenethyl, ethylbenzene, dimethylbenzyl, alphanaphthylmethyl, and beta-naphthylmethyl.

Preferred leaving atoms or groups represented by X in formula (III) include the following atoms or groups in addition to a hydroxyl group and an acetyloxy group.

(a) Halogen atoms such as chlorine, bromine or iodine atom.

(b) Groups of the formula $-OCOR_1$, such as formyl, mono-fluoroacetyloxy, trifluoroacetyloxy, monochloroacetyloxy, propionyloxy, butyryloxy, stearoyloxy, benzoyloxy, 3,5-dimethylbenzoyloxy, and 4-ethylbenzoyloxy.

(c) Groups of the formula $-OR_2$ such as methoxy, ethoxy, phenoxy, 2-pyridyloxy, 2-benzothiazolyloxy, 2-benzoxazolyloxy, trimethylsilyloxy, dimethyl t-butylsilyloxy, methylthio, ethylthio, phenylthio, tolylthio, 2-thiazolinylthio, 2-benzothiazolylthio, 2-benzoxazolylthio, and 2-pyridylthio.

(d) Groups of the formula $-OPO(OR_3)_2$ such as dimethylphosphonoxy, diethylphosphonoxy, and diphenylphosphonoxy.

(e) Groups of the formula $-SOR_3$ such as methylsulfinyl, ethylsulfinyl, propylsulfinyl, phenylsulfinyl and 4-tolylsulfinyl.

(f) Groups of the formula $-SO_2R_3$ such as methylsulfonyl, ethylsulfonyl, propylsulfonyl, phenylsulfonyl, and 4-tolylsulfonyl.

(g) Groups of the formula $-OCO_2R_3$ such as methoxycarbonyloxy, ethoxycarbonyloxy, propoxycarbonyloxy, phenoxycarbonyloxy, and 4-tolyloxycarbonyloxy.

(h) Groups of the formula $$-OCON\begin{matrix}R_3\\R_3\end{matrix}$$

such as N,N-dimethylcarbamoyloxy, N,N-diethylcarbamoyloxy, N,N-dipropylcarbamoyloxy, N,N-diphenylcarbamoyloxy, and N-phenyl-N-ethylcarbamoyloxy, (i) Groups of the formula $$-\overset{\oplus}{N}\begin{matrix}R_3\\-R_3\\R_3\end{matrix}Hal^\ominus$$

such as trimethylammonium bromide, triethylammonium iodide and diphenylethylammonium bromide.

(j) Groups of the formula $$-\overset{\oplus}{S}\begin{matrix}R^3\\\\R^3\end{matrix}Hal^\ominus$$

such as dimethylsulfonium bromide, diethylsulfonium iodide, dipropylsulfonium bromide, and phenylethylsulfonium bromide.

When the compound of formula (III) is used in an isolated form, n in formula (III) is preferably 15.

In the compound of formula (IV) to be reacted with the compound of formula (III), Z represents a group of the formula $-CH_2OH$ or its functional precursor group. The functional precursor groups include hydroxymethyl and aldehyde groups protected by protective groups which can be easily split off by such treatments as hydrolysis or hydrogenolysis. The aldehyde group, after deprotection, can be converted to a hydroxymethyl group by subjecting it to mild reducing conditions, for example reduction with a complex metal hydride such as sodium borohydride, lithium borohydride, lithium aluminum hydride, sodium aluminum hydride.

Specific examples of such functional precursor groups are shown below.

(1) Groups of the formula $-CH_2O-R_4$ wherein $R_4$ represents a lower alkyl group, an aralkyl group having 7 to 11 carbon atoms, an aliphatic or alicyclic ether residue having 1 to 8 carbon atoms, or a silyl group of the formula $$-Si\begin{matrix}R_{51}\\-R_{52}\\R_{53}\end{matrix}$$

in which each of $R_{51}$, $R_{52}$, and $R_{53}$ represents a lower alkyl group, a phenyl group, a tolyl group or a xylyl group. Examples are as follows:

$-CH_2OCH_3$, $-CH_2OC_2H_5$, $-CH_2OC_3H_7$, $-CH_2OC_4H_9$, $-CH_2OC_5H_{11}$, $-CH_2OCH_2OCH_3$, $-CH-$ $_2OCH_2OC_2H_5$, —$CH_2OC_2H_4OCH_3$, —$CH_2OC_2$-$H_4OChd\ 2H_5$, —$CH_2OC_3H_6OCH_3$, —$CH_2OCH_3$-$H_6OC_2H_5$, —$CH_2OC_2H_4OC_2H_4OCH_3$, —$CH_2OCH_2$—$OC_2H_4OCH_3$,

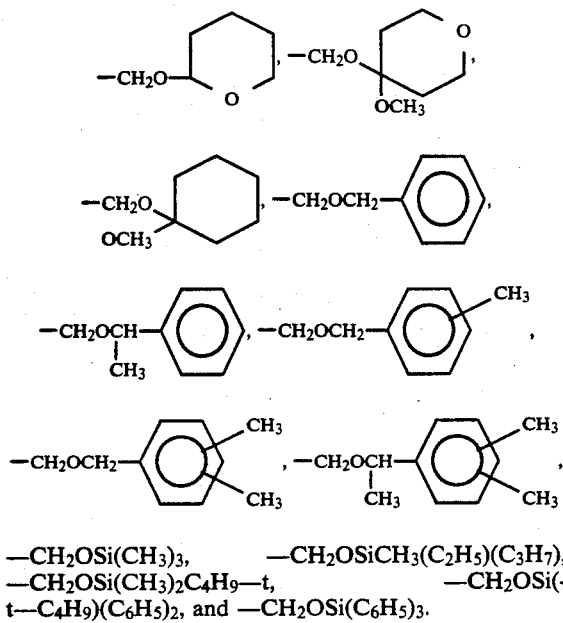

—$CH_2OSi(CH_3)_3$, —$CH_2OSiCH_3(C_2H_5)(C_3H_7)$, —$CH_2OSi(CH_3)_2C_4H_9$—t, —$CH_2OSi($-t—$C_4H_9)(C_6H_5)_2$, and —$CH_2OSi(C_6H_5)_3$.

(2) Groups of the formula

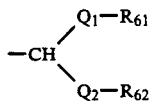

wherein $Q_1$ and $Q_2$ each represent an oxygen or sulfur atom, and $R_{61}$ and $R_{62}$ each represent a lower alkyl group, or when taken together, represent a lower alkylene group.

Examples are as follows:

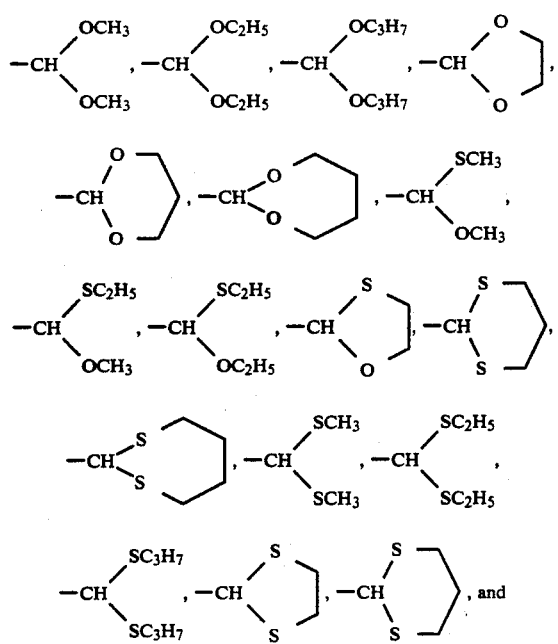

-continued

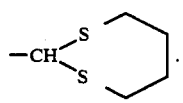

Most of the compounds of formula (IV) are known, and those which are novel can be easily produced in accordance with the methods for producing the known compounds.

The reaction between the compound of formula (III) and the compound of formula (IV) can be carried out by methods known per se. For example, the reaction can be carried out in an inert organic solvent. Typical examples of the solvent are ethers such as by diethyl ether, diisopropyl ether, dioxane, tetrahydrofuran, dimethoxyethane, and diethylene glycol dimethyl ether. It is also possible to use a mixture of such an ether with a small amount of a hydrocarbon such as hexane and benzene, or hexamethylphosphoramide. Tetrahydrofuran is an especially suitable solvent.

The ratio between the compounds of formula (III) and formula (IV) is not critical, and can be broadly varied depending upon the types of the compound of formula (III) and/or the compound of formula (IV), etc. Generally, the compound of formula (IV) is used in a proportion of 0.5 to 10 moles, preferably 1 to 6 moles, especially preferably 1.5 to 4 moles, per mole of the compound of formula (III).

The reaction can be carried out in the presence or absence of a catalyst.

When no catalyst is used, the reaction is advantageously carried out at a temperature of generally from about 0° C. to the refluxing temperature of the reaction mixture, preferably from about 0° C. to about 80° C. Advantageously, the starting compound of formula (III) is the one in which X represents a halogen atom, —$OPO(OR_3)_2$, an oxazolyloxy group, or a pyridyloxy group.

The catalyst which may be used in the above reaction is, for example, a copper catalyst, a nickel catalyst or a palladium catalyst. Examples of the copper catalyst are copper (I) compounds such as CuCl, CuBr, CuI and CuOAc, and copper (II) compounds such as $Li_2CuCl_4$, $CuCl_2$, $CuBr_2$ $CuI_2$, $Cu(OAc)_2$, and $Cu(CH_3COCH-COCH_3)_2$. Examples of the nickel catalyst are nickel complexes, and nickel (II) compounds such as $NiCl_2$, $NiBr_2$, $NiI_2$, $Ni(NO_3)_2$, and $Ni(CH_3COCHCOCH_3)_2$. Examples of the palladium catalyst are palladium complexes, and palladium (II) compounds such as $PdCl_2$, $Pd(OAc)_2$, $Pd(NO_3)_2$, and $Pd(CH_3COCHCOCH_3)_2$.

When a compound of formula (IV) in which Y is MgHal is used as the starting material, copper (I) or (II) compounds are preferred as the catalyst. When a compound of formula (IV) in which Y is a lithium atom is used as the starting material, copper (I) compounds are preferred as the catalyst. The amount of such a copper catalyst is generally 0.001 to 1.0 equivalent, preferably 0.001 to 0.1 equivalent, per mole of the compound of formula (III) in the case of the former, and 1 to 5 equivalents, preferably 1.2 to 3 equivalents, per mole of the compound of formula (III) in the case of the latter.

The suitable reaction temperature used in the reaction of the compound of formula (III) with the compound of formula (IV) in the presence of the above catalysts is generally from −30° C. to +30° C., preferably from −20° C. to +20° C.

Preferred species of X in the starting compound of formula (III) are acetyloxy,

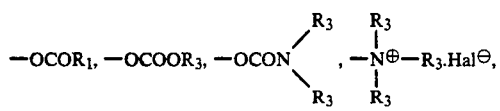

oxazolyloxy, and pyridyloxy.

If the catalyst is used in too large an amount, and/or the reaction is carried out at too high a temperature, an isomer of the compound of formula (V), which is expressed by the following formula

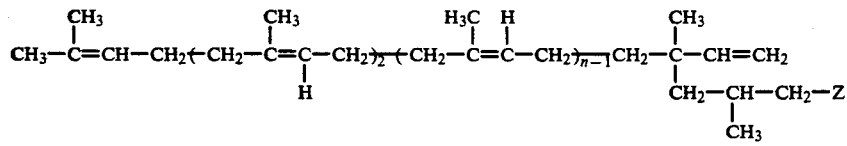

wherein Z and n are as defined above, may occur as a by-product. It is important therefore to select conditions which can minimize formation of this isomer.

By the above reaction, a compound of the following formula

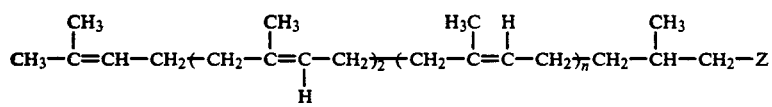

wherein Z and n are as defined hereinabove, can be obtained in good yields. This compound can be separated from the reaction mixture and purified by methods known per se, for example by silica gel or alumina chromatography, fractional dissolution, or molecular distillation.

Removal of the protective group from the compound of formula (V) can be effected by hydrolyzing or hydrogenolyzing it in accordance with methods known per se.

For example, when Z represents —CH$_2$—O—R$_4$ and R$_4$ represents a lower alkyl group, the compound of formula (V) may be deprotected by treating it with iodotrimethylsilane in a solvent such as tetrahydrofuran, chloroform or methylene chloride at room temperature. When R$_4$ in the above formula —CH$_2$—O—R$_4$ represents an aralkyl group, the protective group may be removed by adding a tetrahydrofuran solution of the compound of formula (V) dropwise to a solution of lithium in ethylamine, and after the reaction, decomposing lithium with, for example, a saturated aqueous solution of ammonium chloride. When R$_4$ in the above formula represents an ether residue, the protective group may be removed by dissolving the compound of formula (V), for example, in a mixed solvent of hexane/ethanol (about 1/1), adding pyridinium p-toluenesulfonate (preferably in an amount of about 0.1 to 0.2 equivalent) to the solution, reacting the mixture at about 50° to 60° C. for several hours, and after the reaction, neutralizing the reaction mixture with sodium carbonate or the like. When R$_4$ in the above formula represents a silyl group, the deprotection may be carried out by adding tetra-n-butyl ammonium fluoride (preferably in an amount of about 2-equivalents) to a tetrahydrofuran solution of the compound of formula (V), and stirring the mixture overnight at room temperature.

When Z represents

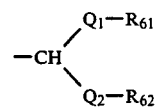

and Q$_1$ and Q$_2$ do not simultaneously represent a sulphur atom, Z may be converted to an aldehyde group (—CHO) by treating the compound of formula (V) with dilute hydrochloric acid (preferably about 10% HCl), etc. in a solvent such as terahydrofuran or isopropanol. When Q$_1$ and Q$_2$ in the above group simultaneously

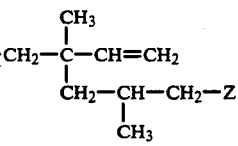

represent sulfur atoms, Z may be converted to the aldehyde group by adding at least an equivalent of HgCl$_2$, CdCO$_3$ and a small amount of water to an acetone solution of the compound of formula (V) and reacting them at room temperature for several hours.

The aldehyde group so converted can be converted to a hydroxymethyl group (—CH$_2$OH) by reducing it under mild reducing conditions, for example reducing it with a complex metal hydride such as sodium borohydride, lithium borohydride, lithium aluminum hydride or a sodium aluminum hydride. The reduction can be carried out by methods known per se. For example, when sodium borohydride is used as the reducing agent, the reaction is desirably carried out at about 0° C. to room temperature in a solvent such as alcohol, tetrahydofuran or ether. When lithium borohydride, lithium aluminum hydride or sodium aluminum hydride is used as the reducing agent, the reducing reaction is advantageously carried out at about −30° C. to room temperature in an anhydrous solvent such as anhydrous diethyl and ether or tetrahydrofuran.

After the reducing reaction, the reaction mixture is treated with water, alcohol, ethyl acetate, etc. to decompose the excess of the reducing agent, and separated and purified in a usual manner to give the desired alcohol [the compound of formula (V) in which Z is hydroxymethyl group] in high yields.

The mammalian dolichols synthesized by the above procedure are useful as valuable biologically active compounds in the fields of medicines and cosmetics.

Compounds of formula (III) in which X represents a leaving atom or group other than the hydroxyl and acetyloxy groups, that is, polyprenyl compounds of the following formula

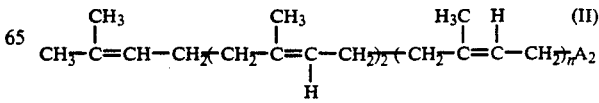

wherein $A_2$ represents a halogen atom or a group of the formula

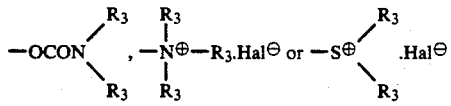

in which $R_1$ represents a hydrogen atom, a methyl group substituted by 1 to 3 fluorine or chlorine atoms, an alkyl or alkenyl group having 2 to 18 carbon atoms, an aryl group having 6 to 10 carbon atoms or an aralkyl group having 7 to 11 carbon atoms, $R_2$ represents a lower alkyl group, a lower alkenyl group, an aryl group having 6 to 10 carbon atoms, a pyridyl group, a thiazolyl group, a thiazolinyl group, or an oxazolyl group, $R_3$ represents a lower alkyl group, an aryl group having 6 to 10 carbon atoms, or an aralkyl group having 7 to 11 carbon atoms, Q represents an oxygen or sulfur atom, and Hal represents a halogen atom;

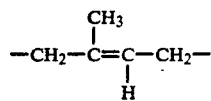

represents a trans-isoprene unit;

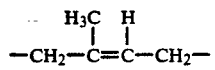

represents a cis-isoprene unit; and n is an integer of 11 to 19, are novel compounds not described in the prior literature. Conversion of the compound of formula (I) to the compound of formula (II), that is, the conversion of $A_1$ in formula (I) to $A_2$ in formula (II), can be performed by methods known per se. Some examples are shown below.

(1) Compounds of Formula (II) in which $A_2$ Is a Halogen Atom

This compound can be obtained by halogenating a compound of formula (I) in which $A_1$ represents a hydroxyl group with a halogenating agent such as a phosphorus trihalide or a thionyl halide. The halogenation may be carried out in a solvent such as hexane or diethyl ether in the absence or presence of a base such as pyridine or triethylamine at a temperature of about $-20°$ C. to about $+50°$ C. by adding the above halogenating agent dropwise.

(2) Compound of Formula (II) in which $A_2$ represents $-OCOR_1$

This compound can be produced by esterification or ester-exchange reaction of a compound of formula (I) in which $A_1$ represents a hydroxyl group. The esterification can be carried out, for example, by reacting the compound of formula (I) with a desired acid anhydride or halide (preferably in an amount of about 1 to about 5 equivalents) in the presence of about 1 to about 10 equivalents of pyridine at a temperature of about $-30°$ C. to about $+50°$ C.

(3) Compound of Formula (II) in which $A_2$ Is $-OR_2$

This compound can be obtained by the reaction of an alcohol or thiol of formula $R_2OH$ with the compound of formula (II) in which $A_2$ represents a halogen produced by the method described in paragraph (1) above, in the presence of a base. A compound of formula (II) in which $A_2$ is $-OR_2$ and Q is an oxygen atom can also be obtained by the reaction of a halide of formula $R_2Hal$ (in which Hal is a halogen atom) with the compound of formula (I) in which $A_1$ is a hydroxyl group.

Generally, the above reaction can be carried out by treating the starting compound with the alcohol or thiol or the halide in a solvent such as dimethyl formamide or tetrahydrofuran in the presence of a base such as sodium hydride or n-butyl lithium at room temperature or under cooling.

(4) Compound of Formula (II) in which $A_2$ Represents $-OPO(OR_3)_2$

This compound can be obtained by reacting a compound of formula (I) in which $A_1$ represents a hydroxyl group with a phosphorochloridate of the formula $ClPO(OR_3)_2$ in a solvent such as chloroform or methylene chloride in the presence of an approximately equivalent or larger amount of pyridine at a temperature of usually about $0°$ C. to room temperature.

(5) Compound of Formula (II) in which $A_2$ Represents $-SOR_3$

This compound can be produced by oxidizing the compound of formula (II) in which $A_2$ represents $-SR_2$ produced as described in paragraph (3) above, with a slight excess of an oxidizing agent such as sodium periodate or aqueous hydrogen peroxide. The oxidation can usually be carried out at room temperature in aqueous methanol, aqueous acetone, etc.

(6) Compound of Formula (II) in which $A_2$ Is $-SO_2R_3$

This compound can be obtained by reacting a compound of formula (II) in which $A_2$ is a halogen atom produced as described in paragraph (1) above, with a compound of the formula $R_3SO_2Na$ in a solvent such as dimethyl formamide or tetrahydofuran at room temperature to about $70°$ C.

(7) Compound of Formula (II) in which $A_2$ Is $-OCO_2R_3$

This compound can be obtained by reacting at compound of formula (I) in which $A_1$ is a hydroxyl group with a haloformate ester of the formula $HalCO_2R_3$ in the presence of a base such as pyridine.

(8) Compound of Formula (II) in which $A_2$ Is

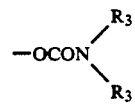

This compound can be produced by reacting a compound of formula (I) in which $A_1$ represents a hydroxyl group with a carbamoyl halide of the formula

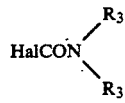

at a temperature of about 0° C. to room temperature in a suitable solvent in the presence of a base such as butyllithium.

(9) Compound of Formula (II) in which $A_2$ is

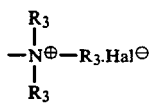

This compound can be obtained by reacting the compound of formula (II) in which $A_2$ is halogen (Hal) produced as described in paragraph (1) above, with a large excess of an amine of the formula

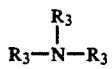

generally at room temperature.

(10) Compound of Formula (II) in which $A_2$ is

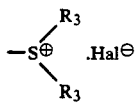

This compound can be produced by reacting the compound of formula (III) in which $A_2$ is $-SR_3$ produced as described in paragraph (3) above, with an alkyl halide of the formula $R_3Hal$, or by reacting the compound of formula (II) in which $A_2$ is a halogen produced as described in paragraph (1) above, with a sulfide of the formula $R_3-S-R_3$.

The following examples illustrate the present invention more specifically.

In these examples, IR analysis was carried out by using a liquid film for oily products and a KBr tablet for solid products. The NMR analysis was carried out by using TMS as an internal standard. The results of Field Desorption Mass Spectrometry (FD-MASS) analysis was corrected for $^1H$, $^{12}C$, $^{14}N$, $^{16}O$, $^{19}F$, $^{28}Si$, $^{31}P$, $^{32}S$, $^{35}Cl$, $^{79}Br$.

EXAMPLE 1

Five kilograms (in the undried state) of the yellowed leaves of Ginkgo biloba collected in Tokyo from late autumn to early winter were crushed into small fragments by a mixer, and then extracted with 100 liters of a mixed solvent of petroleum ether/acetone (4:1 by volume) at about 20° C. The extract was washed with water and dried over anhydrous sodium sulfate. The solvent was distilled off to give about 100 g of a residue. One liter of n-hexane was added to the residue to dissolve n-hexane-soluble components. The solution was filtered, and the filtrate was concentrated and subjected tossilica gel column chromatography using n-hexane/diethyl ether (95/5 by volume) as an eluent to separte a fraction having an Rf value of 0.52 as determined by silica gel thin-layer chromatography (TLC plate silica gel 60F$_{254}$ precoated, layer thickness of 0.25 mm, made by Merck Co.; developed 10cm) using a mixed solvent of n-hexane/ethyl acetate (9/1 by volume) as a developing solvent. Thus, about 17 g of anooily product was obtained. In the above thin-layer chromatography, solanesyl acetate had an Rf of 0.41.

The oily product was heated at 65° C. for 2 hours together with 200 ml of methanol, 20 ml of water and 10 g of sodium hydroxide. Methanol was then distilled off, and 300 ml of diethyl ether was added to the residue to perform extraction. The ethereal layer was washed with about 50 ml of water five times, and dried over anhydrous sodium sulfate. The solvent was distilled off to give 10.3 g of an oily product. The oily product was found to be a polyprenol fraction having a purity of more than 95%. This product was subjected to high-performance liquid chromatography using $\mu$-Bondapak-$C_{18}$ (silica gel surface-treated with a $C_{18}$ hydrocarbon compound) as a packing material, a mixed solvent of acetone/methanol (90/10 by volume) as a developing solvent and a differential refractometer as a detector, and the area proportions of the individual peaks in the resulting chromatography were determined. The results are shown in Table 5.

The individual components were separated from the above oily product (containing more than 95% of polyprenols) by using a high-performance liquid chromatography column ($C_{18}$ type) RD18-10 for semipreparative chromatography (made by Merck Co.) and a mixed solvent of acetone/methanol (90/10 by volume) as a developing solvent. By mass spectroscopy, infrared absorption spectroscopy, $^1$H-NMR spectroscopy and $^{13}$C-NMR spectroscopy, these compounds were determined to be polyprenols having the structure represented by general formula (I).

The results of FD-MASS of these components and their $\delta$ values in $^1$H-NMR spectra are summarized in Table 2. The $\delta$ values of these components in $^{13}$C-NMR spectra are summarized in Table 3.

In the $^1$H-NMR data, (b) represents a broad signal; (d), a doublet signal; and (t), a triplet signal.

TABLE 2

| $n$ (number of cis-isoprene units) | FD-MASS (m/e) | | $^1$H-NMR $\delta$ (ppm) | | | |
|---|---|---|---|---|---|---|
| | Found | Cald. | =CHCH$_2$OH | =CH | —CH$_2$OH | —CH$_2$— |
| 11 | 970 | 970 | 5.44 (t) | 5.13 (b) | 4.08 (d) | 2.04 (b) |
| 12 | 1038 | 1038 | 5.44 (t) | 5.12 (b) | 4.08 (d) | 2.04 (b) |
| 13 | 1106 | 1106 | 5.43 (t) | 5.12 (b) | 4.08 (d) | 2.04 (b) |
| 14 | 1174 | 1174 | 5.44 (t) | 5.12 (b) | 4.08 (d) | 2.04 (b) |
| 15 | 1242 | 1242 | 5.44 (t) | 5.13 (b) | 4.08 (d) | 2.04 (b) |
| 16 | 1310 | 1310 | 5.44 (t) | 5.14 (b) | 4.08 (d) | 2.04 (b) |
| 17 | 1378 | 1378 | 5.44 (t) | 5.13 (b) | 4.08 (d) | 2.04 (b) |
| 18 | 1446 | 1446 | 5.43 (t) | 5.13 (b) | 4.08 (d) | 2.05 (b) |
| 19 | 1514 | 1514 | 5.44 (t) | 5.13 (b) | 4.08 (d) | 2.04 (b) |

$^1$H-NMR $\delta$ (ppm)

TABLE 2-continued

| n (number of cis-isoprene units) | FD-MASS (m/e) Found | FD-MASS (m/e) Cald. | $\underline{H_3C}\diagdown C=C\diagup H$ / $-CH_2$ \ $CH_2OH$ | $\underline{H_3C}\diagdown C=C\diagup H$ / $-CH_2$ \ $CH_2-$ | $\underline{H_3C}\diagdown C=C\diagup CH_2-$ / $-CH_2$ \ $H$ |
|---|---|---|---|---|---|
| 11 | 970 | 970 | 1.74 | 1.68 | 1.60 |
| 12 | 1038 | 1038 | 1.74 | 1.68 | 1.60 |
| 13 | 1106 | 1106 | 1.74 | 1.68 | 1.60 |
| 14 | 1174 | 1174 | 1.74 | 1.68 | 1.60 |
| 15 | 1242 | 1242 | 1.74 | 1.68 | 1.60 |
| 16 | 1310 | 1310 | 1.74 | 1.68 | 1.60 |
| 17 | 1378 | 1378 | 1.74 | 1.68 | 1.60 |
| 18 | 1446 | 1446 | 1.74 | 1.68 | 1.60 |
| 19 | 1514 | 1514 | 1.74 | 1.68 | 1.60 |

TABLE 3

$^{13}$C-NMR δ (ppm)

| n (number of cis-isoprene units) | $\diagdown C=$ / | $=CH-$ | $-\underline{C}H_2OH$ | $CH_3$ / $C=CH$ \ $\underline{C}H_2$ | $CH_3$ / $C=CH$ \ $\underline{C}H_2$ | $CH_3$ / $C=CH$ \ $\underline{C}H_2$ | $CH_3$ / $C=CH$ \ $\underline{C}H_2$ |
|---|---|---|---|---|---|---|---|
| 11 | 135.17 | 125.09 | 59.00 | 39.77 | | 32.27 | 32.04 |
| 12 | 135.17 | 125.10 | 58.99 | 39.78 | | 32.28 | 32.05 |
| 13 | 135.16 | 125.08 | 58.99 | 39.78 | | 32.27 | 32.05 |
| 14 | 135.17 | 125.09 | 59.00 | 39.77 | | 32.27 | 32.04 |
| 15 | 135.15 | 125.12 | 58.99 | 39.78 | | 32.29 | 32.05 |
| 16 | 135.15 | 125.11 | 58.98 | 39.77 | | 32.28 | 32.05 |
| 17 | 135.15 | 125.12 | 59.00 | 39.77 | | 32.29 | 32.05 |
| 18 | 135.16 | 125.10 | 58.98 | 39.77 | | 32.29 | 32.05 |
| 19 | 135.15 | 125.10 | 58.98 | 39.78 | | 32.28 | 32.05 |

$^{13}$C-NMR δ (ppm)

| n (number of cis-isoprene units) | $CH_3$ \ $\underline{C}H_2-$ | $\underline{C}H_3$ | $\underline{C}H_3$ | $\underline{C}H_3$ | $\underline{C}H_3$ |
|---|---|---|---|---|---|
| 11 | 26.47 | 23.42 | 25.67 | 17.64 | 15.98 |
| 12 | 26.47 | 23.42 | 25.66 | 17.64 | 15.98 |
| 13 | 26.48 | 23.42 | 25.67 | 17.65 | 15.99 |
| 14 | 26.47 | 23.42 | 25.66 | 17.64 | 15.97 |
| 15 | 26.49 | 23.42 | 25.65 | 17.65 | 15.99 |
| 16 | 26.49 | 23.42 | 25.65 | 17.64 | 15.98 |
| 17 | 26.49 | 23.41 | 25.66 | 17.65 | 15.99 |
| 18 | 26.48 | 23.41 | 25.64 | 17.64 | 15.99 |
| 19 | 26.49 | 23.42 | 25.65 | 17.65 | 15.98 |

EXAMPLE 2

Ten kilograms (in the undried state) of the non-yellowed leaves of *Ginkgo biloba*, which were collected in Kurashiki City, Japan at the end of October, were dried with hot air at about 40° C. for 24 hours, and then extracted with 80 liters of chlorform at about 15° C. The chloroform was removed from the extract and 5 liters of petroleum ether was added to the concentrate. The insoluble components were separated by filtration. The filtrate was concentrated and chromatographed on a silica gel column using chloroform as an eluent to separate a fraction having an Rf value of 0.50 and 0.19 determined by the same thin-layer chromatography as described in Example 1. Thus, about 37 g of an oily product was obtained. About 400 ml of acetone was added to the oily product to dissolve acetone-soluble components. The resulting residue was filtered, and the filtrate was concentrated. The oily product obtained was heated at 65° C. for 2 hours together with 400 ml of methanol, 40 ml of water and 20 g of sodium hydroxide. Methanol was then distilled off and diethyl ether (500 ml) was added to the resulting product to perform extraction. The ethereal layer was washed with about 100 ml of water five times, and dried over anhydrous sodium sulfate. The solvent was distilled off to give 24.2 g of an oil product.

The oily product was then chromatographed on a column of about 1 kg of silica gel using a mixture of n-hexane/isopropyl ether (90/20 by volume) as an eluent to separate a fraction having an Rf value of 0.19 determined by the same thin-layer chromatography as described in Example 1. Thus, 21.8 g of an oily product was obtained. The oily product was a polyprenol fraction having a purity of more than 95%. The distribution of the molecular weight of the polyprenol fraction measured in the same way as in Example 1 is shown in Table 5.

EXAMPLE 3

Five kilograms (in the undried state) of the leaves of *Ginkgo biloba* collected in Kurashiki City, Japan at the middle of June were treated in the same way as in Example 1 except that the saponification reaction with sodium hydroxide was not carried out. There was obtained 8.7 g of an oily product. The oily product was polyprenyl acetate having a purity of more than 90%. The product was analyzed by the same high-performance liquid chromatography as in Example 1 (except that the developing solvent was changed to a mixed solvent of acetone/methanol in a volume ratio of 70/30), and the area proportions of the individual peaks were determined, and are shown in Table 5.

Furthermore, the individual components of the oily product were separated by using the same high-performance liquid chromatographic column for semipreparative chromatography as used in Example 1 (except that the developing solvent was changed to a mixture of acetone/methanol in a volume ratio of 70/30), and analyzed by FD-MASS, IR, $^1$H-NMR and $^{13}$C-NMR. As a result, these components were determined to be the polyprenyl acetates represented by general formula (I). The area proportions of the individual peaks in the high-performance liquid chromatogram are shown in Table 5, and the FD-MASS analysis values of these components are tabulated below.

| Peak Number | n | FD-MASS (m/e) Found | Calculated |
|---|---|---|---|
| 1 | 11 | 1012 | 1012 |
| 2 | 12 | 1080 | 1080 |
| 3 | 13 | 1148 | 1148 |
| 4 | 14 | 1216 | 1216 |
| 5 | 15 | 1284 | 1284 |
| 6 | 16 | 1352 | 1352 |
| 7 | 17 | 1420 | 1420 |
| 8 | 18 | 1488 | 1488 |
| 9 | 19 | 1556 | 1556 |

EXAMPLE 4

Leaves of *Gingko biloba* collected in Kurashiki City, Japan at the end of October were dried with hot air at about 60° C. for 65 hours, and then divided into 100 g-portions. Each of these portions was dipped in 1 liter of each of the solvents shown in Table 4 to extract the ginkgo leaves at about 25° C. for 7 days. The solvent was distilled off from the extract, and the weight of the resulting concentrate was measured. The measured weight is shown in Table 4 as the total amount of the extract.

Each of these concentrates was dissolved in 200 ml of hexane, and the solution was washed with about 100 ml of a mixture of methanol and water in a volume ratio of 9:1 three times, and dried over anhydrous magnesium sulfate. The solvent was distilled off to give an oily product.

The oily product was heated at 65° C. for 2 hours together with 50 ml of methanol and 1 g of potassium hydroxide. The methanol was then distilled off, and 100 ml of diethyl ether was added to the residue to extract it. The ethereal layer was washed with about 50 ml of a saturated aqueous solution of sodium chloride three times, and dried over anhydrous magnesium sulfate. The solvent was distilled off to give an oily product. The oily product was separated by using 100 g of silica gel and a mixture of hexane and ethyl acetate in a volume ratio of 9:1 to obtain a polyprenol mixture. The weight of the polyprenol mixture is shown in Table 4 as the polyprenol content.

The composition of the resulting polyprenol mixtures was substantially the same as that of the polyprenol mixture obtained in Example 2 irrespective of the type of the solvents used.

TABLE 4

| Solvent | Total amount of the extract (g) | Polyprenol content (g) |
|---|---|---|
| n-Hexane | 4.65 | 0.92 |
| Petroleum ether | 4.60 | 1.06 |
| Benzene | 6.18 | 1.03 |
| Chloroform | 7.82 | 0.98 |
| Carbon tetrachloride | 5.83 | 0.89 |
| Diethyl ether | 6.85 | 1.14 |
| Tetrahydrofuran | 10.51 | 0.97 |
| Methanol | 33.72 | 0.30 |
| Ethanol | 21.71 | 0.69 |
| Isopropyl alcohol | 5.88 | 0.82 |
| Acetone | 8.49 | 1.14 |
| Ethyl acetate | 7.24 | 1.13 |
| Acetone/hexane (20/80) | 6.34 | 1.16 |
| Acetone/hexane (50/50) | 8.68 | 1.34 |
| Acetone/chloroform (20/80) | 8.32 | 1.14 |
| Acetone/chloroform (50/50) | 8.09 | 1.18 |
| Methanol/chloroform (20/80) | 14.60 | 1.10 |
| Methanol/chloroform (50/50) | 22.88 | 1.00 |
| Diethylether/hexane (20/80) | 5.34 | 1.01 |
| Methanol/acetone (20/80) | 17.28 | 1.05 |
| Methanol/acetone (50/50) | 28.30 | 0.90 |

EXAMPLE 5

Ten kilograms of the leaves of *Cedrus deodara* collected in Kurashiki City, Japan at the end of May were worked up the same operation as shown in Example 2 to give 22.1 g of an oily product. The molecular weight distribution of the oily product measured by the same method as shown in Example 1 is shown in Table 5.

TABLE 5

| Peak No. | n | Example 1 | 2 | 3 | 5 |
|---|---|---|---|---|---|
| 1 | 11 | 1.8 | 0.3 | 1.2 | 0.76 |
| 2 | 12 | 3.1 | 1.1 | 4.5 | 2.06 |
| 3 | 13 | 9.4 | 5.9 | 14.4 | 7.00 |
| 4 | 14 | 31.1 | 25.0 | 28.1 | 24.32 |
| 5 | 15 | 35.2 | 39.4 | 33.4 | 38.54 |
| 6 | 16 | 12.7 | 19.2 | 13.0 | 19.22 |
| 7 | 17 | 3.8 | 5.9 | 3.8 | 5.19 |
| 8 | 18 | 1.7 | 1.8 | 1.2 | 1.39 |
| 9 | 19 | 1.2 | 0.8 | 0.4 | 0.54 |
| Average of n | | 14.6 | 15.0 | 14.5 | 14.8 |
| Total of n = 14, 15, 16 | | 79.0% | 84.2% | 75.0% | 82.1% |

EXAMPLE 6

Synthesis of polyprenyl acetate 1.24 g of polyprenol of general formula (III) in which n is 15 and X is —OH and 1.0 g of pyridine were dissolved in dry diethyl ether, and 1.2 g of acetic anhydride was added dropwise to the solution at room temperature. After the addition, the mixture was stirred overnight at room temperature. The reaction mixture was washed with a saturated aqueous solution of sodium chloride, and dried over anhydrous magnesium sulfate. The diethyl ether was distilled off to give a pale yellow viscous liquid. The product was purified by silica gel column chromatography using hexane/ethyl acetate as an eluent to give 1.08 g of a slightly yellow liquid. IR analysis of this liquid showed that the absorption at about 3,300 cm$^{-3}$ attributed to the OH group of the starting polyprenol disappeared, and absorptions at 1745 cm$^{-1}$ and 1255 cm$^{-1}$ attributed to —OCOCH$_3$ newly appeared. In NMR analysis, the signal (doublet, δ=4.08) assigned to —CH₂OH of the starting polyprenol disappeared, and a new signal (doublet, δ=4.55) assigned to CH₂OCCH₃ was observed. The signal to be assigned to —CH₂OCOCH₃ was seen to overlap the signal (δ=2.04) assigned to

FD-MASS analysis gave m/e=1284. From these data, the resulting liquid was determined to be polyprenyl acetate of general formula (III) in which n is 15 and X is —OCOCH₃.

A polyprenyl acetate in which n is other than 15, and a polyprenol acetate mixture in which n distributes arbitrarily between 11 and 19 were synthesized by a similar operation to that described above.

EXAMPLE 7

Synthesis of polyprenyl bromide 12.4 g of polyprenol of general formula (III) in which n is 15 and X is —OH and 1 ml of pyridine were added to 200 ml of n-hexane. To the resulting solution was added dropwise 2.0 g of phosphorus tribromide under an atmosphere of nitrogen. After the addition, the mixture was stirred overnight at room temperature under an atmosphere of nitrogen. The n-hexane solution was put in a separating funnel, washed with about 50 ml of water ten times, and then dried over anhydrous magnesium sulfate. The n-hexane was distilled off to give 12.0 g of a slightly yellow liquid product. When this product was analyzed by NMR spectroscopy, the signal (doublet, δ=4.08) assigned to the —CH₂OH group of the starting polyprenol disappeared, and a signal (doublet, δ=3.91) assigned to —CH₂Br appeared newly. FD-MASS analysis of this liquid product gave m/e=1304. From these analytical data, the above product was determined to be polyprenyl bromide of general formula (II) in which n is 15 and A₂ is Br.

By a similar operation to that described above, a polyprenyl bromide in which n is other than 15, and a polyprenyl bromide mixture in which n distributes arbitrarily between 11 and 19 synthesized.

0.66 g of the above polyprenol bromide (n=15) was dissolved in 10 ml of dimethyl formamide, and 1.0 g of anhydrous sodium acetate was added. The mixture was stirred overnight at about 50° C. Then, about 50 ml of diethyl ether was added, and the mixture was filtered. The filtrate was washed with about 20 ml of water ten times, and dried over anhydrous magnesium sulfate. The solvent was distilled off to give 0.58 g of a pale yellow liquid product. The product was identical in NMR spectrum data and m/e values in FD-MASS analysis with the polyprenyl acetate (n=15) obtained in Example 6, and was therefore determined to be polyprenyl acetate of formula (III) in which n is 15 and X is —OCOCH₃.

EXAMPLE 8

Synthesis of polyprenyl chloride 12.4 g of polyprenol of general formula (III) in which n is 15 and y is —OH and 1.0 ml of pyridine were added to 200 ml of n-hexane. To the resulting solution was added dropwise 1.5 g of thionyl chloride at room temperature under an atmosphere of nitrogen. After the addition, the mixture was further stirred at room temperature for 2 hours. The reaction mixture was then worked up in the same way as in Example 7 to give 11.2 g of a pale yellow liquid. IR analysis of the resulting liquid showed that the absorption attributed to the —OH group of the starting polyprenol disappeared. NMR analysis showed that the signal assigned to —CH₂OH of the starting polyprenol disappeared, and a signal (doublet, δ3.95) assigned to —CH₂Cl newly appeared. The FD-MASS analysis gave m/e=1260. From these analytical data, the above product was determined to be polyprenyl chloride of general formula (II) in which n is 15 and A₂ is Cl.

By a similar operation to that described above, a polyprenyl chloride in which n is other than 15 and a polyprenyl chloride mixture in which n distributes arbitrarily between 11 and 19 were synthesized.

EXAMPLE 9

Synthesis of polyprenol formate 0.8 ml of acetic anhydride and 2 ml of 99% formic acid were mixed under ice cooling, and the mixture was stirred at room temperature for 2 hours. To the resulting mixture was added 1.24 g of polyprenol of general formula (III) in which n is 15 and X is —OH. The mixture was stirred under ice cooling for one hour. The resulting reaction mixture was poured into water, and stirred for 30 minutes. It was then extracted with diethyl ether. The ethereal layer was well washed with water and then with a saturated aqueous solution of sodium chloride, and then dried over anhydrous magnesium sulfate. The ether was distilled off to give 0.48 g of a yellow liquid. This liquid was very unstable. The IR analysis of this product showed that the absorption attributed to the OH group of the starting polyprenol disappeared, and an absorption attributed to the —OCOH group appeared at 1725 cm⁻¹ and 1160 cm⁻¹. In the NMR analysis of the product, a signal (singlet, δ=7.90) assigned to the —OCOH group was observed. From these analytical data, the product was determined to be a compound of formula (II) in which n is 15 and A₂ is —OCOH.

A polyprenol formate in which n is other than 15 and a polyprenol formate mixture in which n distributes arbitrarily between 11 and 19 were synthesized by a similar operation to that described above.

EXAMPLE 10

Synthesis of polyprenol trifluoroacetate 1.24 g of polyprenol of general formula (III) in which n is 15 and X is —OH and 1.0 g of pyridine were dissolved in 10 ml of methylene chloride, and 0.5 g of trifluoroacetic anhdyride was added dropwise at 0° to 5° C. The mixture was stirred at room temperature for 30 minutes. The reaction mixture was poured into water and extracted with diethyl ether. The ethereal layer was washed successively with dilute hydrochloric acid, water and a saturated aqueous solution of sodium chloride, and dried over anhydrous magnesium sulfate. The solvent was distilled off to give 0.83 g of a yellow liquid. The IR analysis of this liquid showed that the absorption attributed to the OH group of the starting polyprenol disappeared, and an absorption attributed to trifluoroacetate appeared newly at 1790 cm⁻¹, 1210 cm⁻¹ and about 1140 cm⁻¹. In the NMR analysis, the signal assigned to —CH₂OH of the stating polyprenol disappeared, and a new signal (doublet, δ=4.72) assigned to —CH$_2$OCOCF$_3$ was observed. The FD-MASS analysis gave m/e=1338. From these analytical data, this product was determined to be a compound of general formula (II) in which n is 15 and A$_2$ is OCOCF$_3$.

A polyprenyl trifluoroacetate in which n is other than 15 and a polyprenyl trifluoroacetate mixture in which n distributes arbitrarily between 11 and 19 were synthesized by a similar operation to that described above.

EXAMPLE 11

Synthesis of polyprenyl monochloroacetate 1.24 g of polyprenol of general formula (III) in which n is 15 and X is OH and 1.0 g of pyridine were dissolved in 10 ml of methylene chloride, and 0.4 g of monochloroacetic anhydride was added dropwise at 0° to 5° C. The mixture was stirred overnight at room temperature. Then, the reaction mixture was worked up in the same way as in Example 10 to give 1.30 g of a pale yellow liquid. The liquid product was further purified by silica gel column chromatography using hexane/ethyl acetate as an eluent to give 1.25 g of a liquid. The IR analysis of the resulting liquid showed that the absorption attributed to the OH group of the starting polyprenol disappeared, and an absorption attributed to C=O appeared at about 1750 cm$^{-1}$. In the NMR spectrum, the signal assigned to —CH$_2$OH disappeared, and a signal (doublet, δ4.57) assigned to —CH$_2$OCOCH$_2$Cl and a signal (singlet, δ=3.92) assigned to —OCOCH$_2$CL newly appeared. The FD-MASS analysis gave m/e=1318. From these analytical data, the liquid product was determined to be a compound of general formula (II) in which n is 15 and A$_2$ is —OCOCH$_2$Cl.

A polyprenyl monochloroacetate in which n is other than 15, and a polyprenyl monochloroacetate mixture in which n distributes arbitrarily between 11 and 19 were synthesized by a similar operation to that described above.

EXAMPLE 12

Synthesis of polyprenyl propionate

The same operation as in Example 6 was repeated except that 1.53 g of propionic anhydride was used instead of the acetic anhydride. There was obtained 1.02 g of a slightly yellow liquid. The IR analysis of the liquid showed that the absorption attributed to the —OH group of the starting polyprenol disappeared, and an absorption attributed to —OCOC$_2$H$_5$ appeared at 1740 cm$^{-1}$ and 1250 cm$^{-1}$. In the NMR spectrum, the signal assigned to —CH$_2$OH of the starting polyprenol disappeared, and a signal (doublet, δ4.56) assigned to —CH$_2$OCOC$_2$H$_5$ was observed. The FD-MASS analysis gave m/e=1298. From these analytical data, the liquid was determined to be a compound of general formula (II) in which n is 15 and A$_2$ is —OCOC$_2$H$_5$.

A polyprenyl propionate in which n is other than 15, and a polyprenyl propionate mixture in which n distributes arbitrarily between 11 and 19 were synthesized by a similar operation to that described above.

EXAMPLE 13

Synthesis of polyprenyl oleate (1) 1.24 g of polyprenol of general formula (III) in which n is 15 and X is —OH, 0.5 g of methyl oleate and 0.01 g of sodium hydride were dissolved in 50 ml of toluene, and the solution was heated at 110° C. for 24 hours under an atmosphere of nitrogen. The reaction solution was cooled to room temperature, washed with a saturated aqueous solution of sodium chloride, and dried over anhydrous magnesium sulfate. The solvent was distilled off to give a yellow liquid. The liquid was purified by silica gel column chromatography using hexane/ethyl acetate as an eluent to give 0.48 g of a colorless viscous liquid. The IR analysis of the liquid showed that the absorption attributed to the OH group of the starting polyprenol disappeared. The FD-MASS analysis gave m/e=1506. From these analytical data, the liquid was determined to be a compound of general formula (II) in which n is 15 is A$_2$ is —OCO-(-CH$_2$-)$_7$CH=CH-(-CH$_2$-)$_7$CH$_3$.

(2) 1.17 g of a polyprenol of general formula (III) in which n is 14 and X is —OH, 0.3 g of methyl oleate and 0.05 g of potassium hydroxide were dissolved in 50 ml of toluene, and the solution was heated at 110° C. for 8 hours under an atmospheric of nitrogen. After the reaction, the reaction mixture was cooled to room temperature, washed with water and dried. The solvent was distilled off to give 1.2 g of a pale yellow liquid. By the same analyses as above, this product was determined to be a compound of formula (II) in which n is 14 and A$_2$ is —OCO-(-CH$_2$-)$_7$CH=CH-(-CH$_2$-)$_7$CH$_3$.

EXAMPLE 14

Synthesis of polyprenyl stearate

Polyprenol of general formula (III) in which n is 15 and X is OH and methyl stearate were subjected to ester-exchange reaction in the same way as in Example 13-(2) except that 0.3 g of methyl stearate was used instead of 0.3 g of methyl oleate. There was obtained 1.2 g of a pale yellow liquid. FD-MASS analysis gave m/e=1508 which showed that this product was a polyprenyl compound of general formula (II) in which n is 15 and A$_2$ is —OCO—(CH$_2$)$_{16}$CH$_3$.

EXAMPLE 15

Synthesis of polyprenyl benzoate

Benzoyl chloride (0.28 g) was added to a mixture of 1.24 g of polyprenol of general formula (III) in which n is 15 and X is —OH and 10 ml of pyridine at room temperature, and the mixture was stirred overnight at room temperature. The reaction mixture was poured into about 150 ml of water, and extracted with diethyl ether. The ethereal layer was washed with a saturated aqueous solution of sodium chloride, dilute hydrochloric acid, water, an aqueous solution of sodium bicarbonate and again a saturated aqueous solution of sodium chloride, and dried over anhydrous magnesium sulfate. The ether was distilled off to give a yellow liquid. The yellow liquid was purified by silica gel column chromatography using hexane/ethyl acetate as an eluent to give 0.92 g of a slightly yellow liquid. The IR spectrum of the resulting liquid showed that the absorption attributed to the OH group of the starting polyprenol disappeared, and an absorption attributed to the ester linkage appeared at 1715 cm$^{-1}$ and 1270 cm$^{-1}$. The FD-MASS analysis gave m/e=1346. From these analytical data, this produce was determined to be a compound of general formula (II) in which n is 15 and A$_2$ is —OCOC$_6$H$_5$.

By a similar operation to that described above, a polyprenyl benzoate in which n is other than 15 and a polyprenyl benzoate mixture in which n distributes arbitrarily between 11 and 19 were synthesized.

EXAMPLE 16-1

Synthesis of polyprenyl methyl ether 1.24 g of polyprenol of general formula (III) in which n is 15 and X is —OH was dissolved in 10 ml of a 1:1 mixture of anhydrous diethyl ether and hexane, and 0.69 ml (1.1 millimoles) of a 1.6M hexane solution of n-butyllithium was added dropwise at 0° C. The mixture was stirred for 10 minutes, and then 156 mg (1.1 millimoles) of methyl iodide was added. After additional stirring for 30 minutes, the reaction mixture was poured into water, and extracted with hexane. The hexane layer was washed with a saturated aqueous solution of sodium chloride and dried over anhydrous magnesium sulfate. The solvent was distilled off to give a yellow liquid. The liquid was purified by silica gel column chromatography using hexane/ethyl acetate as an eluent to give 1.14 g of a slightly yellow liquid. The IR analysis of the purified liquid showed that the absorption attributed to the OH group of the starting polyprenol disappeared, and an absorption attributed to the ether linkage appeared at 1120 l $cm^{-1}$, 1100 $cm^{-1}$ and 1080 $cm^{-1}$. In the NMR spectrum, a signal assigned to —$OCH_3$ appeared at $\delta=3.27$. The FD-MASS analysis gave m/e=1256. From these analytical data, the liquid product was determined to be a compound of general formula in which n is 15 and $A_2$ is —$OCH_3$.

By a similar operation to that described above, a polyprenyl methyl ether in which n is other than 15 and a polyprenyl methyl ether mixture in which n distributes arbitrarily between 11 and 19 were synthesized.

EXAMPLE 16-2

Synthesis of polyprenyl phenyl ether 168 mg of finely divided potassium hydroxide and 310 mg of phenol were dissolved in 30 ml of dimethoxyethane warmed to about 60° C., and 1.30 g of polyprenyl bromide of general formula (II) in which n is 15 and $A_2$ is Br was added. The mixture was heated under reflux for 6 hours. The reaction mixture was cooled, poured into water, and extracted with diethyl ether. The ethereal layer was washed with a 5% aqueous solution of sodium hydroxide twice and then with a saturated aqueous solution of sodium chloride, and then dried over anhydrous magnesium sulfate. The solvent was distilled off to give a yellow liquid. The liquid was purified by silica gel column chromatography using hexane as an eluent to give 0.42 g of a slightly yellow liquid. The IR analysis of the resulting liquid showed that an absorption attributed to phenyl ether appeared at 1600 $cm^{-1}$, 1580 $cm^{-1}$ and 1220 $cm^{-1}$. In the NMR spectrum, the signal (doublet, $\delta=3.91$) assigned to —$CH_2Br$ of the starting polyprenyl bromide disappeared, and a signal (doublet, $\delta=4.39$) assigned to —$CH_2$—O—$C_6H_5$ newly appeared. The FD-MASS analysis gave m/e=1318. From these analytical data, the liquid was determined to be a compound of formula (II) in which n is 15 and $A_2$ is —$OC_6H_5$.

By a similar operation to that described above, a polyprenyl phenyl ether in which n is other than 15 and a polyprenyl phenyl ether mixture in which n distributes arbitrarily between 11 and 19 were synthesized.

EXAMPLE 17

Synthesis of polyprenyl 2-pyridyl ether 0.5 g of 50% sodium hydride was added to 25 ml of anhydrous dimethyl formamide, and the mixture was stirred at room temperature for 1 hour. A solution of 12.4 g of a polyprenol in which n is 15 and X is OH in 10 ml of anhydrous dimethyl formamide was added dropwise. After the addition, the mixture was stirred for 1 hour. Then, 1.1 ml of 2-chloropyridine was added, and the mixture was stirred overnight at room temperature. The reaction mixture was poured into about 100 ml of water, and extracted with diethyl ether. The ethereal layer was washed with water, dried and then concentrated to give a yellow liquid product. The liquid product was chromatographed on a silica gel column using hexane/ethyl acetate as an eluent to give 9.9 g of a slightly yellow liquid. The NMR analysis of the liquid showed that the signal (doublet, $\delta=4.08$) assigned to —$CH_2OH$ of the starting polyprenol disappeared, and a signal (doublet, $\delta=4.71$) assigned to —$CH_2O$—0 and a signal (multiplet, $\delta=6.50$–6.72, multiplet $\delta=7.30$–7.52, multiplet, $\delta=8.00$–8.08) assigned to

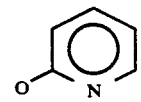

newly appeared. The FD-MASS analysis gave m/e=1319. From these analytical data, this liquid was determined to be polyprenyl 2-pyridyl ether of general formula (II) in which n is 15 and $A_2$ is a 2-pyridyloxy group.

By a similar operation to that described above, a polyprenyl-2-pyridyl ether in which n is other than 15, and a polyprenyl-2-pyridyl ether mixture in which n distributes arbitrarily between 11 and 19 were synthesized.

EXAMPLE 18

Synthesis of polyprenyl 2-benzothiazolyl ether 528 mg of 50% sodium hydride was washed with dry hexane several times under an atmospheric of nitrogen, and 50 ml of anhydrous tetrahydrofuran and 50 ml of anhydrous N,N-dimethylformamide were added. The mixture was stirred. Then, 12.4 g of polyprenol of general formula (III) in which n is 15 and X is —OH was added, and the mixture was stirred at 10° C. for 1 hour. 1.3 ml of 2-chlorobenzothiazole was added dropwise. After the addition, the mixture was stirred at 10° C. for 2 hours and then at room temperature overnight, and thereafter poured into about 200 ml of water. It was extracted with diethyl ether, and the extract was washed with water, dried and concentrated to give 12.5 g of a yellow liquid. In thin-layer chromatography, this compound showed a single spot. The yield of the product was almost quantitative, and no further purification was required. When this liquid was subjected to silica gel column chromatography, it was partially decomposed. The NMR analysis of the liquid showed that the signal (doublet, $\delta=4.08$) assigned to —$CH_2PH$ of the starting polyprenol disappeared, and a signal (doublet, $\delta=5.96$) assigned to —$CH_2O$— and a signal (multiplet, $\delta=6.97$–7.62) assigned to aromatic protons of

appeared newly. The FD-MASS analysis of this liquid gave m/e=1375.

From the above analytical data, this liquid product was determined to be polyprenyl 2-benzothiazolyl ether of general formula (II) in which n is 15 and $A_2$ is

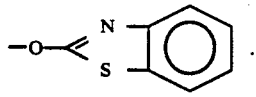

By a similar operation to that described above, a polyprenyl 2-benzothiazolyl ether in which n is other than 15 and a polyprenyl 2-benzothiazolyl ether mixture in which n distributes arbitrarily between 11 and 19 were synthesized.

EXAMPLE 19

Synthesis of polyprenyl t-butyldimethylsilyl ether 1.24 g of polyprenol of general formula (III) in which n is 15 and X is —OH was dissolved in 10 ml of methylene chloride, and 202 mg of triethylamine, 151 mg of t-butyldimethylsilyl chloride and 5 mg of 4-dimethylaminopyridine were added. The mixture was stirred overnight at room temperature. The reaction mixture was poured into water, and extracted with diethyl ether. The ethereal layer was washed with water and a saturated aqueous solution of sodium chloride, and dried over anhydrous magnesium sulfate. The solvent was distilled off to give a liquid. The liquid was purified by column chromatography on a column of silica gel CC-7 (a product of Mallinckrodt) using hexane as an eluent to give 1.30 g of a liquid. The IR analysis of the purified liquid showed that the absorption attributed to the OH group of the starting polyprenol at about 3300 cm$^{-1}$ disappeared. In the NMR spectrum, a signal (singlet, $\delta=0.85$) assigned to —OSiMe$_2$t-Bu was observed. The FD-MASS analysis gave m/e=1356.

From the above analytical data, this liquid was determined to be polyprenyl t-butyldimethylsilyl ether of general formula (II) in which n is 15 and $A_2$ is —OSiMe$_2$t-Bu.

By a similar operation to that described above, a polyprenyl t-butyldimethylsilyl ether in which n is other than 15 and a polyprenyl t-butyldimethylsily ether mixture in which n distributes arbitrarily between 11 and 19 were synthesized.

EXAMPLE 20

Synthesis of polyprenyl methyl sulfide 1.30 g of polyprenyl bromide of general formula (II) in which n is 15 and $A_2$ is Br was dissolved in 1.5 ml of benzene, and 3 ml of a 15% aqueous solution of methylmercaptan sodium salt and 50 mg of benzyl triethyl ammonium chloride were added. The mixture was stirred vigorously overnight at 40° C. The reaction mixture was cooled, and extracted with diethyl ether. The ethereal layer was washed with water and a saturated aqueous solution of sodium chloride, and dried over anhydrous magnesium sulfate. The ether was distilled off to give a yellow liquid. The liquid was purified by silica gel column chromatography using hexane as an eluent to give 0.40 g of a liquid. The NMR analysis of this liquid shows that a signal (singlet, $\delta=1.95$) assigned to S—CH$_3$ and a signal (doublet, $\delta=2.96$) assigned to —CH$_2$SCH$_3$ appeared. The FD-MASS analysis gave m/e=1272. From these analytical data, this liquid was determined to be a compound of general formula (II) in which n is 15 and $A_2$ is SCH$_3$.

By a similar operation to that described above, a polyprenyl methyl sulfide in which n is other than 15 and a polyprenyl methyl sulfide mixture in which n distributes arbitrarily between 11 and 19 were synthesized.

EXAMPLE 21

Synthesis of polyprenyl phenyl sulfide 2.2 g of thiophenol and 2.8 g of potassium carbonate were added to 50 ml of N,N-dimethylformamide, and with stirring at about 20° C., 13.0 g of polyprenylbromide of general formula (II) in which n is 15 and $A_2$ is Br was added dropwise. After the addition, the mixture was stirred overnight at room temperature. The reaction mixture was poured into about 100 ml of water and extracted with hexane. The hexane layer was washed with a 10% aqueous solution of sodium hydroxide and water, and then dried over anhydrous magnesium sulfate. The hexane was distilled off to give a yellow liquid. The yellow liquid was purified by silica gel column chromatography using methylene chloride as an eluent to give 8.6 g of a slightly yellow liquid. The NMR analysis of this liquid showed that a signal (doublet, $\delta=3.91$) assigned to —CH$_2$Br of the starting polyprenyl bromide disappeared, and a signal (doublet, $\delta=3.47$) assigned to a —CH$_2$S— and a signal (multiplet, $\delta=7.05$–7.32) assigned to —SC$_6$H$_5$ newly appeared. The FD-MASS analysis gave m/e=1334.

From these analytical data, the liquid product was determined to be polyprenyl phenyl sulfide of general formula (II) in which n is 15 and $A_2$ is —SC$_6$H$_5$.

By a similar operation to that described above, a polyprenyl phenyl sulfide in which n is other than 15 and a polyprenyl phenyl sulfide mixture in which n distributes arbitrarily between 11 and 19 were synthesized.

EXAMPLE 22

Synthesis of polyprenyl 2-thiazolinyl sulfide 1.35 g of 2-mercaptothiazoline and 0.48 g of 50% sodium hydride were added to 15 ml of N,N-dimethylformimide, and the mixture was stirred at room temperature for 1 hour. A solution of 6.5 g of polyprenyl bromide of general formula (II) in which n is 15 and $A_2$ is Br in 5 ml of N,N-dimethylforminide was added dropwise. After the addition, the mixture was stirred overnight at room temperature. The reaction mixture was poured into about 50 ml of water, and extracted with diethyl ether. The extract was washed with water, dried and concentrated to give a yellow liquid. The liquid was purified by silica gel column chromatography using hexane/ethyl acetate as an eluent to give 2.8 g of a slightly yellow liquid. The NMR analysis of this liquid showed that a signal (doublet, =3.91) assigned to —CH$_2$Br of the starting polyprenyl bromide disappeared, and a signal (doublet, $\delta=3.74$) assigned to —CH$_2$S and signals (triplet, $\delta=3.32$, and triplet, $\delta=4.16$) assigned to

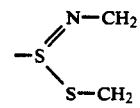

newly appeared. The FD-MASS analysis of this liquid gave m/e=1343. From the above analytical data, this liquid was determined to be polyprenyl 2-thiazolinyl sulfide of general formula (II) in which n is 15 and A₂ is

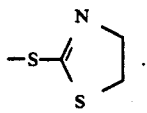

By a similar operation to that described above, a polyprenyl 2-thiazolinyl sulfide mixture were synthesized.

EXAMPLE 23

Synthesis of polyprenyl 2-pyridyl sulfide 1.11 g of 2-mercaptopyridine and 0.48 g of 50% sodium hydride were dissolved in 25 ml of dimethyl formamide, and the mixture was stirred at room temperature for 1 hour. A solution of 6.5 g of polyprenyl bromide of general formula (II) in which n is 15 and A₂ is Br in 5 ml of N,N-dimethylformimide was added dropwise. After the addition, the mixture was stirred overnight at room temperature. The reaction mixture was poured into about 50 ml of water, and extracted with diethyl ether. Then, the diethyl ether layer was washed with water and dried over anhydrous magnesium sulfate. The ether was distilled off to give a yellow liquid. The liquid was purified by silica gel column chromatography using hexane/ethyl acetate as an eluent to give 3.9 g of a slightly yellow liquid. The NMR analysis of this liquid showed that the signal (doublet, δ=3.91) assigned to —CH₂Br of the starting polyprenyl bromide disappeared, and a signal (doublet, δ=3.78) assigned to —CH₂S and a signal (multiplet, δ=6.75–8.35) assigned to —S—C₅H₄N newly appeared. The FD-MASS analysis of this liquid gave m/e=1335.

From the above analytical data, this liquid was determined to be polyprenyl 2-pyridyl sulfide of general formula (II) in which n is 15 and A₂ is —SC₅H₄N.

By a similar operation to that described above, a polyprenyl 2-pyridyl sulfide in which n is other than 15 and a polyprenyl 2-pyridyl sulfide mixture in which n distributes arbitrarily between 11 and 19 were synthesized.

EXAMPLE 24

Synthesis of polyprenyl diethyl phosphate 1.24 g of polyprenol of formula (III) in which n is 15 and X is —OH and 0.16 ml of pyridine were dissolved in 5 ml of methylene chloride, and a solution of 181 mg of diethyl phosphorochloridate in 2 ml of methylene chloride was added dropwise at 0° C. under an atmosphere of nitrogen. The mixture was stirred at 0° C. for 1 hour and then overnight at room temperature. Water was added to the reaction mixture, and it was extracted with diethyl ether. The ethereal layer was washed successively with dilute hydrochloric acid, water, a saturated aqueous solution of sodium bicarbonate, and a saturated aqueous solution of sodium chloride, and dried over anhydrous magnesium sulfate. The ether was distilled off to give 1.35 g of a pale yellow liquid. This liquid showed a single spot in thin-layer chromatography, and no side-reaction was observed. The yield was almost quantitative, and no further purification was required. The IR analysis of this liquid showed that an absorption at 1260 cm⁻¹ attributed to P=O and a broad absorption at 1050 to 940 cm⁻¹ attributed to P—O—C alkyl appeared. In the NMR spectrum, a signal (double doublet, δ=4.38) assigned to

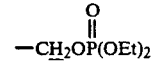

and signals (multiplet, δ=3.8–4.15, and triplet, δ=1.28) assigned to

appeared. The FD-MASS analysis gave m/e=1378.

From these analytical data, the liquid was determined to be a compound of general formula (II) in which n is 15 and A₂ is OP(O)(OEt)₂.

By a similar operation to that described above, a polyprenyl diethyl phosphate in which n is other than 15, and a polyprenyl diethyl phosphate mixture in which n distributes arbitrarily between 11 and 19 were synthesized.

EXAMPLE 25

Synthesis of polyprenyl phenyl sulfoxide 1.33 g of polyprenyl phenyl sulfide of general formula (II) in which n is 15 and A₂ is SC₆H₅ were dissolved in 10 ml of methanol, and a solution of 257 mg of sodium metaperiodate in 5 ml of water was added. The mixture was stirred overnight at room temperature. An aqueous solution of sodium chloride was added to the reaction mixture, and it was extracted with diethyl ether. The ethereal layer was washed with water and a saturated aqueous solution of sodium chloride, and dried over anhydrous magnesium sulfate. The ether was distilled off to give a yellow liquid. The liquid was purified by silica gel column chromatography using hexane/ether as an eluent to give 1.06 g of a purified liquid. The IR analysis of this purified liquid showed that a strong absorption at 1035 cm⁻¹ attributed to sulfoxide which did not exist in the starting polyprenyl phenyl sulfide appeared. In the NMR spectrum, a signal (doublet, δ=3.47) assigned to —CH₂SC₆H₅ of the starting polyprenyl phenyl sulfide disappeared, and a signal (doublet, δ3.35) assigned to —CH₂SOC₆H₅ appeared. The FD-MASS analysis gave m/e=1350. From the above analytical data, this liquid was identified to be polyprenyl phenyl sulfoxide of general formula (II) in which n is 15 and A₂ is —SOC₆H₅.

By a similar operation to that described above, a polyprenyl phenyl sulfoxide in which n is other than 15 and a polyprenyl phenyl sulfoxide mixture in which n distributes arbitrarily between 11 and 19 were synthesized.

EXAMPLE 26

Synthesis of polyprenyl phenyl sulfone 1.30 g of polyprenyl bromide of general formula (II) in which n is 15 and A₂ is Br was dissolved in a mixture of 10 ml of N,N-dimethylformamide and 10 ml of tetrahydrofuran, and 0.33 g of sodium phenylsulfinate was added. The mixture was stirred at room temperature for 17 hours and then at 50° C. for 1 hour. The solvent was removed by a rotary evaporator, and water was added to the reaction mixture, followed by extraction with benzene. The benzene layer was washed with water and dried over anhydrous magnesium sulfate. Removal of the solvent gave a yellow liquid. The liquid was purified by silica gel column chromatography using hexane/ethyl acetate as an eluent to give 0.94 g of a pale yellow liquid. The $^1$H-NMR analysis of this liquid showed that the signal (doublet, $\delta=3.91$) assigned to —CH$_2$Br of the starting polyprenyl bromide disappeared, and a signal (doublet, $\delta=3.77$) assigned to —CH$_2$SO$_2$C$_6$H$_5$ and a signal (multiplet, $\delta=7.31$–7.93) assigned to —SO$_2$C$_6$H$_5$ newly appeared. The FD-MASS analysis of the liquid gave m/e=1366. From these analytical data, this liquid was determined to be a compound of general formula (II) in which n is 15 and A$_2$ is —SO$_2$C$_6$H$_5$.

By a similar operation to that described above, a polyprenyl phenyl sulfone in which n is other than 15 and a polyprenyl phenyl sulfone mixture in which n distributes arbitrarily between 11 and 19 were synthesized.

EXAMPLE 27

Synthesis of polyprenyl ethyl carbonate 12.4 g of polyprenol of general formula (III) in which n is 15 and X is —OH was dissolved in 50 ml of anhydrous pyridine, and with stirring at room temperature, 4.8 ml of ethyl chloroformate was added dropwise. The mixture was stirred overnight at room temperature. The reaction mixture was poured into about 300 ml of water, and extracted with diethyl ether. The ethereal layer was washed with water, dilute hydrochloric acid and water in this order, dried and concentrated to give a yellow liquid. This liquid was chromatographed on a silica gel column using hexane/ethyl acetate as an eluent to give 7.21 g of a slightly yellow liquid. The NMR analysis of this liquid showed that the signal (doublet, $\delta=4.08$) assigned to —CH$_2$OH of the starting polyprenol disappeared, and a signal (doublet, $\delta 4.45$) assigned to —CH$_2$O and signals (triplet, $\delta=1.20$ and quartet, $\delta=4.05$) assigned to

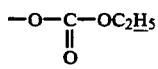

newly appeared. The FD-MASS analysis of the product gave m/e=1314. From these analytical data, the liquid was determined to be polyprenyl ethyl carbonate of general formula (II) in which n is 15 and A$_2$ is

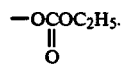

By a similar operation to that described hereinabove, a polyprenyl ethyl carbonate in which n is other than 15 and a polyprenyl ethyl carbonate mixture in which n distributes arbitrarily between 11 and 19 were synthesized.

EXAMPLE 28

Synthesis of polyprenyl dimethyl carbamate 2.48 g of polyprenol of general formula (III) in which n is 15 and X is —OH was dissolved in 10 ml of anhydrous tetrahydrofuran. The solution was cooled to 0° C., and with stirring, 1.4 ml of a 1.6M hexane solution of n-butyllithium was added. At the same temperature, 0.3 ml of dimethylcarbamoyl chloride was added. The mixture was stirred at 0° C. for 30 minutes and then at room temperature for 2 hours. The reaction mixture was poured into about 20 ml of water, and extracted with diethyl ether. The extract was washed with water, dried and concentrated to give a yellow liquid. The liquid was chromatographed on a silica gel column using hexane/ethyl acetate as an eluent to give 2.16 g of a slightly yellow liquid. The NMR analysis of the liquid showed that the signal (doublet, $\delta=4.08$) assigned to —CH$_2$OH of the starting polyprenol disappeared, and a signal (doublet, $\delta=4.42$) assigned to —CH$_2$O and a signal (singlet, $\delta=2.80$) assigned to

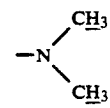

newly appeared. The FD-MASS analysis of this liquid gave m/e=1313. From these analytical data, this liquid was determined to be polyprenyl dimethyl carbamate of general formula (II) in which n is 15 and A$_2$ is

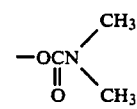

By a similar operation to that described above, a polyprenyl dimethyl carbamate in which n is other than 15 and a polyprenyl dimethyl carbamate mixture in which n distributes arbitrarily between 11 and 19 were synthesized.

EXAMPLE 29

Synthesis of polyprenyl triethyl ammonium bromide 2.6 g of polyprenyl bromide of general formula (II) in which n is 15 and A$_2$ is Br was added to 10 ml of anhydrous triethylamine, and the mixture was left to stand overnight at room temperature. Consequently, a pale yellow waxy material precipitated. The precipitate was separated and washed thoroughly with anhydrous diethyl ether. The solvent was removed under reduced pressure to give 2.35 g of a pale yellow waxy product. The NMR analysis (DMSO-d$_6$) of this product showed that the signal (doublet, $\delta=3.91$) assigned to —CH$_2$Br of the starting polyprenyl bromide disappeared, and a signal (doublet, $\delta=3.77$) assigned to —CH$_2$N and signals (triplet, $\delta=1.14$, and quartet, $\delta=3.22$) assigned to —N(C$_2$H$_5$)$_3$ newly appeared. Since this waxy product was very hygroscopic, its elemental and IR analyses were impossible. FD-MASS analysis was also impossible because the product was an ammonium salt. NMR analysis, however, led to the determination that this waxy product was the desired polyprenyl triethyl ammonium bromide of general formula (II) in which n is 15 and A$_2$ is N$\oplus$(C$_2$H$_5$)$_3$Br$\ominus$.

By a similar operation to that described above, a polyprenyl triethyl amonium bromide in which n is other than 15 and a polyprenyl triethyl ammonium bromide mixture in which n distributes arbitrarily between 11 and 19 were synthesized.

EXAMPLE 30

Synthesis of polyprenyl dimethyl sulfonium bromide 2.6 g of polyprenyl bromide of general formula (II) in which n is 15 and $A_2$ is Br was added to 10 ml of dimethyl sulfide and the mixture was left to stand overnight at room temperature. Consequently, a yellow waxy material precipitated. The precipitate was separated and washed thoroughly with anhydrous diethyl ether, and then the solvent was removed under reduced pressure to give 1.27 g of a yellow waxy product. The NMR analysis of this product showed that the signal (doublet, $\delta=3.91$) assigned to —$CH_2Br$ of the starting polyprenyl bromide disappeared, and a signal (doublet, $\delta=4.15$) assigned to —$CH_2S\oplus<$ and a signal (singlet, $\delta=2.88$) assigned to —$\oplus S(CH_3)_2$ newly appeared. Since this product was highly hygroscopic, its elemental analysis was impossible. FD-MASS analysis was also impossible because the product was a sulfonium salt. The NMR analysis, however, led to the determination that the product was the desired polyprenyl dimethyl sulfonium bromide of general formula (II) in which n is 15 and $A_2$ is —$\oplus S(CH_3)_2 Br\ominus$.

By a similar operation to that described above, polyprenyl dimethyl sulfonium bromide in which n is other than 15 and a polyprenyl dimethyl sulfonium bromide mixture in which n distributes arbitrarily between 11 and 19 were synthesized.

EXAMPLE 31

A three-necked flask purged with argon was charged with 0.316 g (13 millimoles) of magnesium flakes, 0.5 ml of anhydrous terahydrofuran and 0.08 ml of 1,2-dibromoethane, and they were heated by a dryer until vigorous bubbling occurred. A solution of 2.51 g (10 millimoles) of 2-[4-bromo-3-methylbutoxy]-tetrahydro-2H-pyrane in 3.0 ml of anhydrous tetrahydrofuran was added dropwise to the activated magnesium at such a speed that the solvent was just boiled. Then, 60 ml of anhydrous tetrahydrofuran was added to form a Grignard Solution.

Another three-necked flask purged with argon was charged with a solution of 6.42 g (5 millimoles) of the polyprenyl acetate of general formula (III) in which n is 15 and X is —$COCH_3$ produced in the same way as in Example 6 in 15 ml of anhydrous tetrahydrofuran, and 2.0 ml of a 0.1M anhydrous tetrahydrofuran solution of $Li_2CuCl_4$. Then, the Grignard solution prepared as above was added dropwise at 0° C. for 1 hour, and then the mixture was stirred at 0° C. for 2 hours. Thereafter, a saturated aqueous solution of ammonium chloride was added to the reaction mixture to perform hydrolysis, and the product was extracted with diethyl ether. The diethyl ether layer was washed with a saturated aqueous solution of sodium chloride, and dried over anhydrous magnesium sulfate. The solvent was then removed by means of a rotary evaporator to give 7.95 g of a pale yellow liquid. By silica gel thin-layer chromatography (hexane/ethyl acetate=97/3 as a developing solvent), this liquid was found to have a main spot at Rf=0.35. The FD-MASS analysis of the pale yellow liquid did not give m/e=1284 which showed the presence of the starting polyprenyl acetate, but gave m/e=1396 as a main peak which showed the presence of the desired compound of general formula (V) in which Z is a tetrahydro-2H-pyranyloxymethyl group.

The pale yellow liquid was then dissolved in 40 ml of hexane, and 0.13 g (0.5 millimole) of pyridinium p-toluenesulfonate and 20 ml of ethanol were added. The solution was heated at 55° C. for 3 hours with stirring. The reaction mixture was cooled, and then neutralized with 0.21 g of sodium carbonate. The solvent was distilled off by a rotary evaporator. The resulting concentrate was dissolved in diethyl ether, washed with a saturated aqueous solution of sodium bicarbonate and then with a saturated aqueous solution of sodium chloride, and then dried over anhydrous magnesium sulfate. The solvent was removed by means of a rotary evaporator. The remaining oily substance was heated at 150° C. and 0.5 torr for 30 minutes to remove low-boiling components. The remaining oil was chromatographed on a silica gel column using hexane/ethyl acetate (9/1) as an eluent to give 5.64 g of a colorless transparent liquid. By silica gel thin-layer chromatography (hexane/ethyl acetate=9/1 as a developing solvent), this liquid showed a single spot at Rf=0.79. By the analytical data shown below, this liquid was determined to be the desired compound of general formula (V) in which n is 15 and Z is —$CH_2OH$.

FD-MASS: m/e=1312 (calculated 1312)

IR ($cm^{-1}$): 830, 1060, 1376, 1440, 2850, 2920, 3320.

$^{13}C$-NMR (ppm/intensity): 135.365/430, 135.229/3567, 135.005/349, 134.937/290, 131.210/213, 125.071/5242, 124.993/499, 124.448/505, 124.282/463, 124.214/445, 61.241/551, 40.029/541, 39.757/683, 37.548/582, 32.245/5500, 32.021/456, 29.316/528, 26.825/492, 26.699/548, 26.426/5166, 35.677/542, 25.308/567, 23.430/6330, 19.557/548, 17.679/353, 16.006/640.

$^1H$-NMR (ppm, signal form, proton ratio): 5.10 (b, 18H), 3.66 (m, 2H), 2.03 (b, 70H), 1.68 (s, 48H), 1.60 (s, 9H, 1.80–1.10 (m, 5H), 0.91 (d, 3H).

In the IR analysis an absorption at 907 $cm^{-1}$ was not detected, and in $^1H$-NMR analysis, a signal at $\delta=5.78$ ppm (double doublet) was not detected at all. These absorptions show the formation of the isomerization product described hereinabove.

The 2-[4-bromo-3-methylbutoxy]tetrahydro-2H-pyran used in the above procedure was synthesized by the following method.

16.7 g of 4-bromo-3-methylbutanol was dissolved in 200 ml of anhydrous methylene chloride, and with ice cooling, 10.0 g of dihydropyran was added dropwise. After the addition, the mixture was stirred at room temperature for 2 hours, and then the solvent was distilled off. The residue was purified by silica gel column chromatography using hexane/ethyl acetate as an eluent to give 16.2 g of 2-[4-bromo-3-methylbutoxy]-tetrahydro-2H-pyran. The NMR spectrum of this product was as follows:

$\delta$ ppm: 1.00 (doublet, 3H), 1.20–2.20 (multiplet, 9H), 3.20–3.90 (multiplet, 6H), 4.53 (broad, 1H).

EXAMPLES 32 TO 34

Example 31 was repeated except that each of the polyprenyl compounds (n=15) shown in Table 6 was used instead of the polyprenyl acetate used in Example 31. The results are shown in Table 6.

EXAMPLE 35

The procedure of Example 31 before the reaction with pyridinium p-toluenesulfonate was repeated except that 4-bromo-3-methylbutyl benzyl ether was used instead of the 2-[4-bromo-3-methylbutoxy]-tetrahydro-2H-pyran and CuBr was used instead of $Li_2CuCl_4$. The resulting liquid product was heated at 130° C. and 0.5 torr for 30 minutes to remove low-boiling components. Thus, 6.75 g of a pale yellow liquid was obtained. This liquid was then purified by silica gel column chromatography using hexane/isopropyl ether (97/3 by volume) as an eluent to give 5.33 g of a slightly yellow liquid. In silica gel thin-layer chromatography (hexane/diisopropyl ether=95/5 by volume as a developing solvent), this liquid gave a single spot at Rf=0.59. From the following analytical data, this liquid product was determined to be a compound of general formula (V) in which n is 15 and Z is —$CH_2OCH_2C_6H_5$.

FD-MASS: m/e=1402

IR ($cm^{-1}$): 698, 735, 840, 1100, 1378, 1450, 1662, 2840, 2930, 2970

$^1$H-NMR ($\delta$ ppm, signal form, proton number ratio): 7.28 (s, 5H), 5.07 (b, 18H), 4.42 (s, 2H), 3.45 (t, 2H), 2.04 and 2.00 (s, 70H), 1.62 (s, 48H), 1.50 (s, 9H), 1.22 (b, 5H), 0.80 (b, 3H).

A three-necked flask purged with argon was cooled with ice-water, and 10 ml of anhydrous ethylamine was introduced into the flask. Then, 0.10 g (15 mg-atom) of lithium was added, and the contents of the flask were stirred at 0° C. for 10 minutes to give a blue solution. A solution of the pale yellow liquid obtained as above in anhydrous tetrahydrofuran was added dropwise over 10 minutes to the resulting blue solution. The mixture was stirred at 0° C. for 30 minutes, and diethyl ether and an aqueous saturated solution of ammonium chloride were added to perform hydrolysis. The ethereal layer was washed with 1N hydrochloric acid, a saturated aqueous solution of sodium bicarbonate and a saturated aqueous solution of sodium chloride, and dried over anhydrous magnesium sulfate. The solvent was distilled off. The remaining liquid product was purified by silica gel column chromatography using hexane/ethyl acetate (9/1 by volume) as an eluent to give 4.80 g of a colorless transparent liquid. The Rf value in silica gel thin-layer chromatography, FD-MASS, IR, $^{13}$C-NMR and $^1$H-NMR data of this product were identical with those of the liquid product obtained in Example 31. In the IR analysis, an absorption at 907 $cm^{-1}$ was not detected at all, and in the $^1$H-NMR analysis, a signal at $\delta=5.78$ was not detected at all.

EXAMPLES 36 TO 44

Example 35 was repeated except that each of the polyprenyl compounds (n=15) indicated in Table 6 was used instead of the polyprenyl acetate used in Example 35. The results are shown in Table 6. In Examples 42 and 43, a weak absorption at 907 $cm^{-1}$ in the IR spectrum, and a weak signal at $\delta=5.78$ ppm in the $^1$H-NMR were detected. This led to the determination that a small amount of the undesired isomer existed.

EXAMPLES 45 TO 48

Example 35 was repeated except that each of the metal compounds indicated in Table 6 was used instead of cuprous bromide. The results are shown in Table 6.

EXAMPLE 49

A three-necked flask purged with argon was charged with 0.474 g (19.5 millimoles) of magnesium flakes, 0.5 ml of anhydrous tetrahydrofuran and 0.08 ml of 1,2-dibromoethane. They were heated by a dryer until vigorous bubbling occurred. A solution of 3.86 g (15 millimoles) of 4-bromo-3-methylbutyl benzyl ether in 4.5 ml of anhydrous tetrahydrofuran was added dropwise to the activated magnesium at such a speed that the solvent was just boiling. After the addition, the mixture was stirred at 70° C. for 30 minutes, and 25 ml of anhydrous tetrahydrofuran was added to form a Grignard solution.

Another three-necked flask purged with argon was charged with 1.43 g (7.5 millimoles) of anhydrous cuprous iodide and 40 ml of anhydrous tetrahydrofuran. The flask was then cooled to −30° C. in a dry ice-acetone bath. The Grignard solution prepared as above was added dropwise to the resulting suspension at −30° C., and after the addition, the mixture was stirred at −30° C. for 20 minutes.

A solution of 6.42 g (5 millimoles) of the polyprenyl acetate of general formula (III) in which n is 15 and X is —$OCOCH_3$ produced in the same way as in Example 6 in 10 ml of anhydrous tetrahydrofuran was added dropwise at −30° C. to the resulting white suspension. The reaction mixture was gradually brought to room temperature, and stirred at room temperature for 10 hours.

Then, a saturated aqueous solution of ammonium chloride was added to the reaction mixture to perform hydrolysis. It was then extracted with diethyl ether. The ethereal layer was washed with a saturated solution of ammonium chloride and dried over anhydrous magnesium sulfate. The solvent was distilled off. The resulting pale yellow liquid was heated at 130° C. and 0.5 torr for 30 minutes to remove low-boiling components. The residue was purified by silica gel column chromatography using hexane/diisopropyl ether (97/3) as an eluent to give 4.63 g of a slightly yellow liquid. This liquid gas a single spot at Rf=0.59 in silica gel thin-layer chromatography (using hexane/diisopropyl ether=95/5 as a developing agent). The FD-MASS analysis of the product gave m/e=1402. These analytical data were identical with those of the compound of general formula (V) in which n is 15 and Z is $CH_2OCH_2C_6H_5$ obtained in Example 35.

The resulting liquid was subjected to a reaction of removing the benzyl group by the same operation as in Example 35. The product was purified by silica gel column chromatography using hexane/ethyl acetate (9/1) as an eluent to give 4.15 g of a colorless clear liquid. The Rf value in silica gel thin-layer chromatography (hexane/ethyl acetate=9/1 as a developing solvent) and the m/e value in FD-MASS of this liquid were identical with those of the compound of general formula (V) in which n is 15 and Z is $CH_2OH$ obtained in Example 31. But a weak absorption was noted at 907 $cm^{-1}$ in IR analysis and $\delta=5.78$ ppm in $^1$H-NMR.

EXAMPLES 50 AND 51

Example 49 was repeated except that each of the polyprenyl compounds (n=15) shown in Table 6 was used instead of the polyprenyl acetate used in Example 49. In both of Examples 50 and 51, the IR analysis and the NMR analysis showed the presence of a small amount of the undesired isomer.

EXAMPLE 52

Example 35 was repeated except that polyprenyl bromide (n=15) was used instead of the polyprenyl acetate, cuprous bromide was not used, and after the addition of the Grignard solution, the reaction was carried out at the refluxing temperature of tetrahydrofuran for 9 hours instead of carrying it out at 0° C. for 2 hours. The results are shown in Table 6.

EXAMPLES 53 TO 55

Example 52 was repeated except that the other polyprenyl compounds (n=15) indicated in Table 6 were used instead of the polyprenyl bromide. The results are shown in Table 6.

TABLE 6

| | Compound (III) | | Compound (IV) | | | Metal catalyst | | Reaction temp. | Amount of the reaction product | Formation of |
|---|---|---|---|---|---|---|---|---|---|---|
| Example | X | Amount (g) | Y | Z | Amount (g) | Type | Amount | and time | (g) | undesired isomer (*) |
| 31 | OAc | 6.42 | MgBr |  CH₂—O | 2.51 | Li₂CuCl₄ | 0.1M solution 2.0 ml | 0° C. 2 hr | 5.64 | ○ |
| 32 | OCOC₂H₅ | 6.49 | " | " | " | " | " | " | 5.35 | ○ |
| 33 | OCOC₁₇H₂₃ | 7.53 | " | " | " | " | " | " | 3.94 | ○ |
| 34 | OCOC₆H₅ | 6.73 | " | " | " | " | " | " | 5.23 | ○ |
| 35 | OAc | 6.42 | " | CH₂OCH₂C₆H₅ | 2.57 | CuBr | 0.029 g | " | 4.80 | ○ |
| 36 | OCO₂C₂H₅ | 6.36 | " | " | " | " | " | " | 4.26 | ○ |
| 37 | OCON(CH₃)₂ | 6.56 | " | " | " | " | " | " | 4.10 | ○ |
| 38 | OCOCH₂Cl | 6.59 | " | " | " | " | " | " | 3.93 | ○ |
| 39 | OCOCF₃ | 6.69 | MgBr | CH₂OCH₂C₆H₅ | 2.57 | CuBr | 0.029 g | 0° C. 2 hr | 3.80 | ○ |
| 40 | OCOH | 6.35 | " | " | " | " | " | " | 0.52 | ○ |
| 41 | N⊕(C₂H₅)₃Br⊖ | 7.03 | " | " | " | " | " | " | 2.76 | ○ |
| 42 | S⊕(CH₃)₂Br⊖ | 6.83 | " | " | " | " | " | " | 4.23 | ○ |
| 43 | Br | 7.61 | " | " | " | " | " | " | 4.41 | △ |
| 44 | SO₂C₆H₅ | 6.83 | " | " | " | " | " | " | 1.31 | △ |
| 45 | OAc | 6.42 | " | " | " | CuI | 0.038 | " | 4.75 | ○ |
| 46 | OAc | 6.42 | " | " | " | Cu(AcAc)₂ (**) | 0.052 | " | 4.62 | ○ |
| 47 | OAc | 6.42 | " | " | " | NiCl₂-(dppf) (***) | 0.136 | " | 0.79 | ○ |
| 48 | OAc | 6.42 | " | " | " | PdCl₂-(dppf) | 0.146 | " | 0.27 | ○ |
| 49 | OAc | 6.42 | " | " | " | CuI | 1.43 | " | 4.15 | △ |
| 50 | (pyridine-SH) | 6.67 | MgBr | CH₂OCH₂C₆H₅ | 2.57 | CuI | 1.43 | room temp. 10 hr. | 2.96 | △ |
| 51 | (thiazoline) | 6.71 | " | " | " | " | " | room temp. 10 hr. | 4.23 | △ |
| 52 | Br | 7.61 | " | " | " | None | None | Refluxing of THF 9 hrs. | 0.72 | ○ |
| 53 | (benzoxazole-2-thione) | 6.87 | " | " | " | " | " | " | 3.35 | ○ |

TABLE 6-continued

| | Compound (III) | | Compound (IV) | | | Metal catalyst | | Reaction temp. | Amount of the reaction product | Formation of |
|---|---|---|---|---|---|---|---|---|---|---|
| Example | X | Amount (g) | Y | Z | Amount (g) | Type | Amount | and time | (g) | undesired isomer (*) |
| 54 | [pyridin-2-yloxy structure] | 6.59 | " | " | " | " | " | " | 3.18 (****) | ○ |
| 55 | OPO(OC$_2$H$_5$)$_2$ | 6.89 | " | " | " | " | " | " | 3.01 | Δ |

(*)○: The absence of the isomer was ascertained by IR and $^1$H—NMR analyses;
Δ: The presence of a small amount of the isomer was ascertained by the same analyses.
(**): AcAc = acetylacetonato group.
(***): dppf =1,1'-diphenylphosphinoferrocene.
(****): The reaction was carried out using MgBr$_2$ (1.84 g).

EXAMPLE 56

A three-necked flask purged with argon as charged with 1.7 g (0.25 gram-atom) of lithium and 40 ml of anhydrous ether, and a solution of 25.1 g (100 millimoles) of 2-[4-bromo-3-methylbutoxy]-tetrahydro-2H-pyran in 20 ml of anhydrous diethyl ether was first added in a small amount. After ascertaining that heat was generated, the mixture was cooled to 0° C. and the remainder of the solution was added dropwise. After the addition, the mixture was stirred at 10° C. for 2 hours.

Separately, 990.6 mg (5.2 millimoles) of anhydrous cuprous iodide and 20 ml of anhydrous diethyl ether were put in another three-necked flask purged with argon, and the lithium reagent solution (corresponding to 10 millimoles) prepared as above was added dropwise at $-10°$ C. over 10 minutes. The mixture was stirred further for 15 minutes at this temperature. A solution of 3.21 g (2.5 millimoles) of polyprenyl acetate of general formula (III) in which n is 15 and X is —OCOCH$_3$ in 15 ml of anhydrous diethyl ether was added dropwise at $-10°$ C. over 20 minutes. Furthermore, at this temperature, the mixture was stirred for 1 hour. The reaction mixture was hydrolyzed by adding a saturated aqueous solution of ammonium chloride, and extracted with diethyl ether. The ethereal layer was washed with a saturated aqueous solution of sodium chloride, and dried over anhydrous magnesium sulfate. The solvent was removed by means of a rotary evaporator to give 5.09 g of a pale yellow liquid. This product had a main spot at Rf=0.35 in silica gel thin-layer chromatography (hexane/ethyl acetate=97/3 as a developing solvent). The FD-MASS analysis of this product gave m/e=1396.

The liquid product was reacted with pyridinium p-toluenesulfonate and then worked up in the same way as in Example 31 to give 2.12 g of a colorless clear liquid. The results of its silica gel thin-layer chromatography, FD-MASS, IR and $^1$H-NMR analyses were the same as those obtained in Example 31.

EXAMPLE 57

Example 56 was repeated except that polyprenyl phenylsulfoxide in which n is 15 and X is S(O)C$_6$H$_5$ was used instead of the polyprenyl acetate. Thus, 1.15 g of a colorless clear liquid was obtained. The results of its silica gel thin-layer chromatography and FD-MASS analysis were the same as those obtained in Example 56.

EXAMPLE 58

Example 56 was repeated except that polyprenyl phenyl sulfone in which n is 15 and X is S(I)$_2$C$_6$H$_5$ was used instead of the polyprenyl acetate. Thus, 1.38 g of a colorless clear liquid was obtained. The results of its silica gel thin-layer chromatography and FD-MASS analysis were the same as those obtained in Example 56.

EXAMPLE 59

A three-necked flask purged with argon was charged with 1.7 g (0.25 gram-atom) of lithium and 40 ml of anhydrous diethyl ether, and a solution of 25.1 g (100 millimoles) of 2-[4-bromo-3methylbutoxy]-tetrahydro-2H-pyran in 20 ml of anhydrous diethyl ether was added in a small amount. After ascertaining that heat was generated, the mixture was cooled to 0° C., and the remainder of the solution was added dropwise. After the addition, the mixture was stirred at 10° C. for 2 hours.

Another three-necked flask purged with argon was charge with 3.80 (2.5 millimoles) of polyprenyl bromide of general formula (III) in which n is 15 and X is Br and 10 ml of anhydrous diethyl ether, and the lithium reagent solution (corresponding to 10 millimoles) prepared as above was added dropwise at 0° C. over 10 minutes, and then the mixture was stirred for 10 hours at room temperature.

The reaction mixture was then hydrolyzed by adding a saturated aqueous solution of ammonium chloride, and extracted with diethyl ether. The ethereal layer was washed with a saturated aqueous solution of sodium chloride and dried over anhydrous magnesium sulfate. The solvent was removed by means of a rotary evaporator to give 5.46 g of a pale yellow liquid.

The liquid was reacted with pyridinium p-toluenesulfonate and worked up in the same was as in Example 31 to give 0.44 g of a colorless clear liquid. The results of its silica gel thin-layer chromatography and FD-MASS analysis were the same as those obtained in Example 31.

EXAMPLE 60

(A) A three-necked flask purged with argon was charged with .7 g (0.25 gram-atom) of lithium and 40 ml of anhydrous diethyl ether and a solution of 25.1 g (100 millimoles) of 2-[4-bromo-3-methylbutoxy]-tetrahydro-2H-pyran in 20 ml of anhydrous diethyl ether was added in a small amount. After ascertaining that heat was generated, the mixture was cooled to 0° C. and the remainder of the solution was added dropwise. After the addition, the mixture was stirred at 10° C. for 2 hours.

(B) A solution of 3.11 g (2.5 millimoles) of polyprenol of general formula (III) in which n is 15 and X is —OH in 5 ml of anhydrous diethyl ether was put in another three-necked flask purged with argon, and at 0° C. a diethyl ether solution of methyl lithium (1.3 moles/liter, 1.9 ml, 2.5 millimoles) was added dropwise. After the addition, the mixture was stirred at 0° C. for 20 minutes.

Then, the other three-necked flask purged with argon was charged with 0.48 g (2.5 millimoles) of anhydrous cuprous iodide and 6 ml of anhydrous tetrahydrofuran, and the diethyl ether solution prepared in (B) was added dropwise at room temperature. After the addition, the mixture was stirred at room temperature for 30 minutes, and then cooled to $-65°$ C. in a dry ice-acetone bath.

Then, the lithium reagent solution (corresponding to 10 millimoles) prepared in (A) above was added dropwise at this temperature, and subsequently, a solution of 1.24 g (2.5 millimoles) of N,N-methylphenylaminotriphenyl phosphonium iodide in 13 ml of anhydrous N,N-dimethyl formamide was added dropwise. After the addition, the mixture was stirred at $-65°$ C. for 1 hour, and gradually brought to room temperature. It was then stirred at room temperature for 2 hours.

The reaction mixture was hydrolyzed by adding a saturated aqueous solution of ammonium chloride, and extracted with diethyl ether. The ethereal layer was washed with 0.2N hydrochloric acid and dried over anhydrous magnesium sulfate. The solvent was removed by means of a rotary evaporator and the residue was mixed with 50 ml of hexane. Then, the precipitated triphenyl phosphine oxide was filtered off and the filtrate was concentrated to give 3.49 g of a pale yellow liquid.

The liquid was reacted with pyridinium p-toluenesulfonate and worked up in the same way as in Example 31 to give 2.10 g of a colorless clear liquid. The results of silica gel thin-layer chromatography, FD-MASS, IR, $^1$H-NMR and $^{13}$C-NMR analyses were the same as those obtained in Example 31.

EXAMPLE 61

A thee-necked flask purged with argon was charged with 0.316 g (13 millimoles) of magnesium flakes, 0.5 ml of anhydrous tetrahydrofuran and 0.08 ml of 1,2-dibromoethane and they were heated by a dryer until vigorous bubbling occurred. Then, a solution of 4.05 g (10 millimoles) of 4-(t-butyl-diphenyl silyloxy)-2-methylbutyl bromide in 5.0 ml of anhydrous tetrahydrofuran was added dropwise to the activated magnesium at such a speed that the solvent was just boiling. After the addition, the mixture was stirred at 70° C. for 30 minutes. Then, 60 ml of anhydrous tetrahydrofuran was added to form a Grignard solution.

Another three-necked flask purged with argon was charged with a solution of 6.42 g (5 millimoles) of polyprenyl acetate of general formula (III) in which n is 15 and X is —OCOCH$_3$ in 15 ml of anhydrous tetrahydrofuran and an anhydrous tetrahydrofuran solution of Li$_2$CuCl$_4$ (0.1 M solution, 2.0 ml). The Grignard solution prepared as above was added dropwise at 0° C. for 1 hour, and the mixture was stirred at 0° C. for 2 hours. Then, the reaction mixture was hydrolyzed by adding a saturated aqueous solution of ammonium chloride, and extracted with diethyl ether. The ethereal layer was washed with a saturated aqueous solution of sodium chloride, and dried over anhydrous magnesium sulfate. The solvent was removed by means of a rotary evaporator to give an oily product. The oily product was heated at 130° C. and 0.5 torr for 30 minutes to remove low-boiling components. The residue was then purified by silica gel column chromatography using hexane/ethyl acetate as an eluent to give 4.27 g of a colorless clear liquid. The FD-MASS analysis of this liquid was m/e=1550. This liquid was then dissolved in 30 ml of tetrahydrofuran, and with stirring at room temperature, 5 g of tetra-n-butyl ammonium fluoride was added in small portions. The mixture was then stirred at room temperature for 2 hours. The tetrahydrofuran was distilled off, and about 50 ml of diethyl ether was added. The ethereal layer was washed with a saturated aqueous solution of sodium chloride and dried over anhydrous magnesium sulfate. The diethyl ether was distilled off to give a liquid. The liquid was purified by silica gel column chromatography using hexane/ethyl acetate (9/1) as an eluent to give 3.82 g of a colorless clear liquid. In silica gel thin-layer chromatography (hexane/ethyl acetate=9/1 as a developing solvent), this liquid gave the same Rf value as the compound obtained in Example 31. The results of its FD-MASS, IR, $^1$H-NMR and $^{13}$C-NMR analyses were the same as those obtained in Example 31. Accordingly, this liquid was determined to be a compound of general formula (V) in which n is 15 and Z is —CH$_2$OH.

The 4-(t-butyl-diphenyl-silyloxy)-2-methylbutyl bromide used above was synthesized by the following procedure.

16.7 g of 4-bromo-3-methylbutanol was dissolved in 500 ml of anhydrous methylene chloride, and 13.2 g of triethylamine and 500 mg of 4-dimethylaminopyridine were added. At room temperature, 33.0 g of t-butyldiphenylsilyl chloride was added dropwise. After the addition, the mixture was stirred overnight at room temperature, poured into water, and extracted with diethyl ether. The ethereal layer was thoroughly washed with a saturated aqueous solution of sodium chloride, and dried over anhydrous magnesium sulfate. The diethyl ether was distilled off to give an oily product. The oily product was purified by chromatography using a column of silica gel CC-7 (a product of Mallinckrodt) and hexane/diethyl ether as an eluent to give 38.1 g of a colorless clear liquid. The IR analysis of this liquid showed that the absorption at about 3300 cm$^{-1}$ attributed to the OH group of the starting material disappeared. In its NMR analysis, signals were observed at δ 0.90 (3H, doublet), 1.02 (9H, singlet), 1.1–1.7 (2H, multiplet), 1.7–2.2 (1H, multiplet), 3.22 (doublet, 2H), 3.63 (2H, triplet), 7.1–7.4 (5H, multiplet) and 7.4–7.8 (5H, multiplet). Accordingly, this liquid product was determined to be the desired 4-(t-butyldiphenylsilyloxy)-2-methylbutyl bromide.

EXAMPLE 62

A three-necked flask purged with argon was charged with 0.316 g (13 millimoles) of magnesium flakes, 0.5 ml of anhydrous terahydrofuran and 0.08 ml of 1,2-dibromoethane, and they were heated by a dryer until vigorous bubbling occurred. Then, a solution of 1.81 g (10 millimoles) of 4-methoxy-2-methylbutyl bromide in 3.0 ml of tetrahydrofuran was added dropwise to the activated magnesium at such a speed that the solvent was just boiled. After the addition, the mixture was stirred at 70° C. for 15 minutes. Then, 60 ml of anhydrous terahydrofuran was added to form a Grignard solution.

Another three-necked flask purged with argon was charged with a solution of 6.42 g (5 millimoles) of polyprenyl acetate of general formula (III) in which n is 15 and X is —OCOCH$_3$ in 15 ml of anhydrous tetrahydrofuran and an anhydrous tetrahydrofuran solution of Li$_2$CuCl$_4$ (0.1 M solution, 2.0 ml), and the Grignard solution prepared as above was added dropwise at 0° C. for 1 hour. The mixture was stirred at 0° C. for 2 hours. Then, the reaction mixture was hydrolyzed by adding a saturated aqueous solution of ammonium chloride, and extracted with diethyl ether. The ethereal layer was washed with a saturated aqueous solution of sodium chloride, and dried over anhydrous magnesium sulfate. The solvent was distilled off by means of a rotary evaporator. The resulting oily product was heated at 130° C. and 0.5 torr for 30 minutes to remove low-boiling components, and then purified by silica gel column chromatography using hexane/ethyl acetate as an eluent to give 4.72 g of a colorless clear liquid. The FD-MASS analysis of this product showed a peak at m/e=1326. Hence, this liquid was determined to be the desired compound of general formula (V) in which n is 15 and Z is —CH$_2$OCH$_3$.

Then, this liquid was dissolved in 10 ml of anhydrous methylene chloride and in an atmosphere of argon, 1.30 g (6.5 millimoles) of iodotrimethylsilane was added at room temperature. The mixture was stirred at room temperature for 10 hours. Then, 1 ml of methanol was added, and the mixture was stirred for 20 minutes. The solvent was removed by means of a rotary evaporator, and the remaining liquid was dissolved in diethyl ether. The ethereal layer was washed with an aqueous solution of sodium bisulfite, an aqueous solution of sodium bicarbonate and an aqueous solution of sodium chloride, and dried over anhydrous magnesium sulfate. The solvent was distilled off, and the resulting liquid product was purified by silica gel column chromatography using hexane/ethyl acetate/=9/1 as an eluent to give 3.28 g of a colorless clear liquid. The Rf value in silica gel thin-layer chromatography (hexane/ethyl acetate=9/1 as a developing solvent), the m/e value in FD-MASS and the IR, $^1$H-NMR and $^{13}$C-NMR data of this liquid were identical with those of the compound of general formula (V) in which n is 15 and Z is —CH$_2$OH obtained in Example 31.

The 4-methoxy-2-methylbutyl bromide was synthesized in the following manner.

30.7 g of 50% sodium hydride was suspended in 400 ml of tetrahydrofuran, and a solution of 50.0 g of 3-methyl-3-buten-1-ol in 50 ml of tetrahydrofuran was added. The mixture was heated under reflux for 2 hours, and under ice cooling, a solution of 90.8 g of methyl iodide in 50 ml of tetrahydrofuran was added dropwise. The mixture was stirred overnight at room temperature. The reaction mixture was poured into water and extracted with diethyl ether. The ethereal layer was washed with water and a saturated aqueous solution of sodium chloride, and dried over anhydrous magnesium sulfate. The solvent was carefully distilled off, and the residue was fractionally distilled under atmospheric pressure to give 66.5 g of a liquid as a fraction boiling at 99° to 102° C. The IR analysis of this liquid showed that the absorption at about 3300 cm$^{-1}$ attributed to the OH group of the starting alcohol disappeared. In its NMR analysis, signals were observed at δ1.69 (singlet, 3H), 2.23 (triplet, 2H), 3.26 (singlet, 3H) 3.57 (triplet, 2H) and 4.71 (broad singlet, 2H). The GC-MASS analysis gave m/e=100. From the above analytical data, this liquid was determined to be 3-methyl-3-butenyl methyl ether.

2.5 g of sodium borohydride was suspended in 320 ml of tetrahydrofuran, and 20.0 g of 3-methyl-3-butenyl methyl ether was added dropwise. Then, 10.1 ml of boron trifluoride-diethyl ether complex was added dropwise at 25° C. The mixture was stirred for 1 hour, and then cooled to 0° C. 42.56 g of bromine and 64.0 g of a 28 wt. % methanol solution of sodium methoxide were added dropwise below 5° C. through two different dropping funnels. The reaction mixture was stirred further at room temperature for 20 minutes, and then 100 ml of a saturated aqueous solution of sodium bicarbonate was added. Water was further added until the white precipitate disappeared. The organic layer was separated. The water layer was extracted with diethyl ether. The organic layers were combined, and washed with a saturated aqueous solution of sodium thiosulfate, a saturated aqueous solution of sodium bicarbonate and a saturated aqueous solution of sodium chloride in this order, and then dried over anhydrous magnesium sulfate. The solvent was distilled off, and the residue was distilled under reduced pressure to give 22.5 g of a colorless clear liquid as a fraction boiling at 60° C./5 mmHg. In the NMR analysis of this liquid, signals were observed at δ0.96 (doublet, 3H), 1.38-2.10 (multiplet, 3H), 3.31 (singlet, 3H), and 3.35-3.60 (multiplet, 4H). From these data, this liquid was determined to be the desired 4-methoxy-2-methylbutyl bromide.

EXAMPLE 63

A three-necked flask purged with argon was charged with 0.316 g (13 millimoles) of magnesium flakes, 0.5 ml of anhydrous tetrahydrofuran and 0.08 ml of 1,2-dibromoethane, and they were heated by a dryer until vigorous bubbling occurred. Then, a solution of 2.11 g (10 millimoles) of 4,4-dimethoxy-2-methylbutyl bromide in 3.0 ml of anhydrous tetrahydrofuran was added dropwise to the activated magnesium at such a speed that the solvent was just boiling. The mixture was then stirred at 70° C. for 30 minutes. Then, 60 ml of anhydrous tetrahydrofuran was added to form a Grignard solution.

Another three-necked flask purged with argon was charged with 6.42 g (5 millimoles) of polyprenyl acetate of general formula (III) in which n is 15 and X is —OCOCH$_3$ and an anhydrous tetrahydrofuran solution of Li$_2$CuCl$_4$ (0.1 M solution, 2.0 ml). The Grignard solution prepared as above was added dropwise at 0° C. for 1 hour. The mixture was then stirred at 0° C. for 2 hours. The reaction mixture was hydrolyzed by adding a saturated aqueous solution of ammonium chloride and extracted with diethyl ether. The ethereal layer was washed with a saturated aqueous solution of sodium chloride, and dried over anhydrous magnesium sulfate. The solvent was distilled off by means of a rotary evaporator to give 7.67 g of a pale yellow liquid. When this liquid was subjected to FD-MASS analysis, the peak at m/e=1284 showing the presence of the starting polyprenyl acetate was very weak, and m/e=1356 showing the desired compound of formula (V) in which n is 15 and Z is —CH(OCH$_3$)$_2$ was detected as a main peak.

The pale yellow liquid was then put in a mixture of 30 ml of tetrahydrofuran and 10 ml of 10% hydrochloric acid, and the mixture was stirred at room temperature for 5 hours. The reaction mixture was subjected to a rotary evaporator to remove tetrahydrofuran, and the residue was extracted with diethyl ether. The ethereal layer was washed with a saturated aqueous solution of sodium chloride, a saturated aqueous solution of sodium bicarbonate and a saturated aqueous solution of sodium chloride in this order, and dried over anhydrous magnesium sulfate. The diethyl ether was distilled off by means of a rotary evaporator to give 7.29 g of a pale yellow liquid. In the FD-MASS analysis of this liquid, m/e=1310 was detected as a main peak. This led to the determination that this liquid was a compound of formula (V) in which n is 15 and Z is —CHO.

This liquid was then dissolved in a mixture of 20 ml of hexane and 10 ml of ethanol, and 1.0 g of sodium borohydride was added at room temperature. The mixture was stirred for 1 hour. The solvent was then removed by means of a rotary evaporator, and about 50 ml of diethyl ether was added to the residue. The ethereal layer was washed with a saturated aqueous solution of sodium chloride, and dried over anhydrous magnesium sulfate. The solvent was removed by means of a rotary evaporator. The remaining oily substance was heated at 150° C. and 0.5 torr for 30 minutes to remove low-boiling components. The remaining oily substance was purified by silica gel column chromatography using hexane/ethyl acetate (9/1) an eluent to give 4.25 g of a colorless clear liquid. The results of its IR, $^1$H-NMR, $^{13}$C-NMR and FD-MASS were identical with those of the compound of general formula (V) in which n is 15 and Z is —CH$_2$OH obtained in Example 31.

The 4,4-dimethoxy-2-methylbutyl bromide used above was synthesized by the following procedure.

20.9 g of ethyl 4-bromo-3-methyl butyrate was dissolved in 400 ml of anhydrous toluene, and the solution was stirred at −78° C. In an atmosphere of nitrogen, diisobutyl aluminum hydride (1 M solution, 120 ml) was added dropwise, and the mixture was stirred at −78° C.

for 30 minutes. Methanol was then added carefully to decompose the excess of the reducing reagent. The product was diluted with 400 ml of diethyl ether, and 100 ml of water was added. The mixture was stirred at room temperature for 2 hours. The solution was filtered through Celite, and the aqueous layer was extracted with diethyl ether. The organic layers were combined, washed with an aqueous solution of sodium chloride, and dried over anhydrous magnesium sulfate. The solvent was distilled off to give 14.8 g of a crude oily product. The IR analysis of this oily product showed that weak absorptions at 2820 and 2720 cm$^{-1}$ and a strong absorption at 1720 cm$^{-1}$, characteristic of the —CHO group, were observed. In the NMR analysis, a signal assigned to —CHO was observed at $\delta = 9.60$.

The crude oily product was dissolved in 300 ml of methanol, and 500 mg of p-toluenesulfonic acid was added. The mixture was stirred at room temperature for 2 hours. The reaction mixture was neutralized by adding sodium bicarbonate, and concentrated under reduced pressure. The residue was poured into water, and extracted with diethyl ether. The ethereal layer was washed with a saturated aqueous solution of sodium chloride, and dried over anhydrous magnesium sulfate. The diethyl ether was distilled off to give 18 g of a crude oily product. The oily product was purified by silica gel column chromatography using hexane/diethyl ether as an eluent to give 17.2 g of a colorless clear liquid. The IR analysis of this liquid showed that the characteristic absorptions at 2820, 2720 and 1720 cm$^{-1}$ attributed to —CHO disappeared, and several absorptions attributed to the acetal appeared at 1200 to 1000 cm$^{-1}$. In the NMR analysis, signals were observed at $\delta 1.00$ (3H, doublet), 1.1–1.7 (2H, multiplet), 1.7–2.0 (1H, multiplet), 3.22 (6H, singlet), 3.31 (2H, multiplet), and 4.32 (1H, triplet). The GC-MASS analysis gave m/e=210. From these analytical data, this liquid was determined to be 4,4-dimethoxy-2-methylbutyl bromide.

EXAMPLE 64

A three-necked flask purged with argon was charged with 0.316 g (13 millimoles) of magnesium flakes, 0.5 ml of anhydrous tetrahydrofuran and 0.08 ml of 1,2-dibromoethane, and they were heated by a dryer until vigorous bubbling occurred. Then, a solution of 2.43 g (10 millimoles) of 4,4-dimethylthio-2-methylbutyl bromide in 3.0 ml of anhydrous tetrahydrofuran was added dropwise to the activated magnesium at such a speed that the solvent was just boiled. After the addition, the mixture wa stirred at 70° C. for 15 minutes. Then, 60 ml of anhydrous tetrahydrofuran was added to form a Grignard solution.

A three-necked flask purged with argon was charged with a solution of 6.42 g (5 millimoles) of polyprenyl acetate of general formula (III) in which n is 15 and X is —OCOCH$_3$ in 15 ml of anhydrous tetrahydrofuran and an anhydrous tetrahydrofuran solution of Li$_2$CuCl$_4$ (0.1 M solution, 2.0 ml). The Grignard solution prepared as above was added dropwise at 0° C. over 1 hour, and the mixture was then stirred at 0° C. for 2 hours. The reaction mixture was hydrolyzed by adding a saturated aqueous solution of ammonium chloride, and extracted with diethyl ether. The ethereal layer was washed with an aqueous solution of sodium chloride, and dried over anhydrous magnesium sulfate. The solvent was distilled off by means of a rotary evaporator. The resulting oily product was heated at 150° C. and 0.3 torr for 30 minutes to remove low-boiling components. The FD-MASS analysis of the remaining yellow liquid showed that a peak was detected at m/e=1388 which showed the presence of the compound of formula (V) in which n is 15 and Z is CH(SCH$_3$)$_2$.

The oily product was dissolved in 20 ml of acetone, and 1 ml of water, 0.25 g of mercuric chloride and 0.25 g of cadmium carbonate were added. The mixture was stirred at room temperature for 25 hours, and further 0.10 g of mercuric chloride and 0.10 g of cadmium carbonate were added, the mixture was stirred for 20 hours further. The precipitate was removed by filtration, and acetone was distilled off. The remaining liquid was dissolved in diethyl ether. The ethereal layer was washed with water, a 10% aqueous solution of potassium iodide, water, and a saturated aqueous solution of sodium chloride in this order, and dried over anhydrous magnesium sulfate. The solvent was distilled off, and the residue was dissolved in 20 ml of hexane and 10 ml of ethanol. To the solution was added 1.0 g of sodium borohydride at room temperature and the mixture was stirred for 1 hour. The solvent was distilled off, and diethyl ether and a saturated aqueous solution of ammonium chloride were added to the residue. The aqueous layer was extracted with diethyl ether. The ethereal layer was washed with a saturated aqueous solution of sodium chloride, and dried over anhydrous magnesium sulfate. The solvent was distilled off, and the remaining oily product was heated at 130° C. and 0.5 torr for 30 minutes to remove low-boiling components. The residue was purified by silica gel chromatography using hexane/ethyl acetate (9/1) as an eluent to give 3.07 g of a colorless clear liquid. The Rf value in silica gel thin-layer chromatography (hexane/ethyl acetate=9/1 as a developing solvent), the m/e value of FD-MASS, and the IR, $^1$H-NMR and $^{13}$C-NMR of this liquid were identical with those of the compound of general formula (V) in which n is 15 and Z is —CH$_2$OH obtained in Example 31.

The 4,4-dimethylthio-2-methylbutyl bromide used above was synthesized by the following procedure.

14.8 g of crude aldehyde obtained by reducing ethyl 4-bromo-3-methylbutyrate was diisobutyl aluminum hydride at —78°-0 C. in anhydrous toluene was dissolved in 200 ml of anhydrous diethyl ether. At 0° C., 21.6 g of methylthiotrimethylsilane was added dropwise, and the mixture was stirred at room temperature for 2 hours. Water was added, and the mixture was extracted with diethyl ether. The ethereal layer was washed with a saturated aqueous solution of sodium chloride, and dried over anhydrous magnesium sulfate. The diethyl ether was distilled off and the resulting liquid was purified by silica gel column chromatography using hexane/diethyl ether as an eluent to give 17.4 g of a colorless clear liquid.

The IR analysis of this liquid showed that absorptions attributed to the starting aldehyde were not observed at 2820, 2720, and 1720 cm$^{-1}$. In the NMR analysis, a signal (triplet, $\delta = 3.83$) assigned to

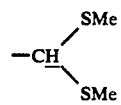

and a signal (singlet, $\delta = 2.08$) assigned to

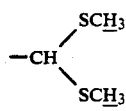

were observed. The GC-MASS analysis gave m/e=242.

From these analytical data, the liquid was determined to be the desired 4,4-dimethylthio-2-methylbutyl bromide.

EXAMPLE 65

Example 35 was repeated except that anhydrous diethyl ether was used instead of the anhydrous tetrahydrofuran. Thus, 4.52 g of a colorless clear liquid was obtained. The Rf value in silica gel thin-layer chromatography (hexane/ethyl acetate=9/1 as an eluent) and the m/e value in FD-MASS of this liquid were identical with those of the compound of general formula (V) in which n is 15 and Z is —CH$_2$OH obtained in Example 35. In the IR analysis, a weak absorption was observed at 907 cm$^{-1}$.

EXAMPLE 66

Example 35 was repeated except that (S)-4-bromo-3-methylbutyl benzyl ether ($[\alpha]_D^{20}$=+6.05°, c=1.10, ethanol) was used instead of the 4-bromo-3-methylbutyl benzyl ether, and the polyprenyl acetate mixture, prepared by the method of Example 6 using the polyprenol mixture in which n distributes between 11 and 19 obtained in Example 2, was used instead of the polyprenyl acetate in which n is 15. There was obtained 4.72 g of a colorless clear liquid.

By high-performance liquid chromatography using Li Chrosorb RP 18-10 (C$_{18}$ type) (a semipreparative high-performance liquid chromatography column made by Merck Co.), a mixture of acetone and methanol (90/10) as an eluent, and a differential refractometer as a detector, nine main peaks were observed. The ratio of the existence of each component was calculated from the area ratio of this chromatogram. The results are shown below.

| Peak No. | n | Ratio of existence | FD-MASS |
|---|---|---|---|
| 1 | 11 | 0.3 | 1040 |
| 2 | 12 | 1.0 | 1108 |
| 3 | 13 | 5.9 | 1176 |
| 4 | 14 | 25.7 | 1244 |
| 5 | 15 | 39.6 | 1312 |
| 6 | 16 | 19.3 | 1380 |
| 7 | 17 | 5.7 | 1448 |
| 8 | 18 | 1.7 | 1516 |
| 9 | 19 | 0.8 | 1584 |

The individual fractions were separated by using the same liquid chromatography, and subjected to FD-MASS analysis. It was confirmed that the respective peaks are attributed to n=11-19. The fractions separated according to the respective peaks were analyzed by IR, $^1$H-NMR and $^{13}$C-NMR, and it was confirmed that the product was the compound of general formula (V) in which n is 11 to 19, and Z is —CH$_2$OH. The compound in which n is 15 and which correspond to peak No. 5 showed quite the same analytical values as the compound obtained in Example 31. The compounds correspond to the other peaks showed absorption signals in IR, $^1$H-NMR and $^{13}$C-NMR at the same positions as the compound correspond to peak No. 5 with some differences in intensity ratios. The resulting liquid product had a specific rotation of $[\alpha]_D^{20}$=+0.51° (neat).

EXAMPLE 67

Example 31 was repeated except that (R)-2-[4-bromo-3-methylbutoxy]-tetrahydro-2H-pyran ($[\alpha]_D^{20}$=−3.61°, c=4.0, chloroform) synthesized by using (R)-4-bromo-3-methylbutanol in accordance with the method described at the end of Example 31 was used instead of the 2-[4-bromo-3-methylbutoxy]-tetrahydro-2H-pyran, and the same polyprenyl acetate mixture as used in Example 66 was used instead of the polyprenyl acetate (n=15). Thus, 5.52 g of a colorless clear liquid was obtained. The liquid was analyzed by high-performance liquid chromatography under the same conditions as in Example 66. The results were the same as in Example 66. The results of its FD-MASS, IR $^1$H-NMR and $^{13}$C-NMR analyses were also the same as in Example 66. The liquid product had a specific rotation of $[\alpha]_D^{20}$=−0.51° (neat).

What we claim is:

1. A polyprenyl compound of the following formula

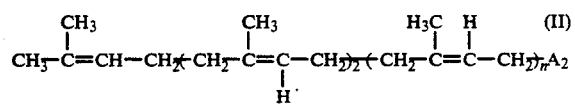

wherein A$_2$ represents a halogen atom or a group of the formula

—OCOR$_1$, —OR$_2$, —OPO(OR$_3$)$_2$, —SOR$_3$, —SO$_2$R$_3$, —OCOOR$_3$,

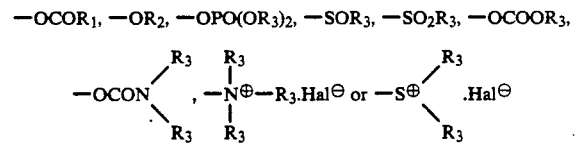

in which R$_1$ represents a hydrogen atom, a methyl group substituted by 1 to 3 fluorine or chlorine atoms, an alkyl or alkenyl group having 2 to 18 carbon atoms, an aryl group having 6 to 10 carbon atoms or an aralkyl group having 7 to 11 carbon atoms, R$_2$ represents a lower alkyl group, a lower alkenyl group, a hydrogen atom an aryl-group having 6 to 10 carbon atoms, a pyridyl group, a thiazolyl group, a thiazolinyl group, or an oxazolyl group, R$_3$ represents a lower alkyl group, an aryl group having 6 to 10 carbon atoms, or an aralkyl group having 7 to 11 carbon atoms, O represents an oxygen or sulfur atom, and Hal represents a halogen atom;

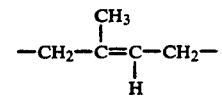

represents a trans-isoprene unit;

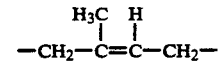

represents a cis-isoprene unit; and n is an integer of 11 to 19.

2. The compound of claim 1 wherein n is 15.

3. The compound of claim 1 wherein R$_2$ represents a halogen atom or —SO$_2$R$_3$ in which R$_3$ is as defined in claim 1.

* * * * *